United States Patent
Tateno et al.

(10) Patent No.: US 9,914,908 B2
(45) Date of Patent: Mar. 13, 2018

(54) METHOD OF INTRODUCING A TOXIN OR DYE INTO MAMMALIAN PLURIPOTENT CELLS USING RBC2LCN

(71) Applicant: National Institute of Advanced Industrial Science and Technology, Tokyo (JP)

(72) Inventors: Hiroaki Tateno, Ibaraki (JP); Yuzuru Ito, Ibaraki (JP); Yasuko Onuma, Ibaraki (JP); Jun Hirabayashi, Ibaraki (JP); Makoto Asashima, Ibaraki (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 79 days.

(21) Appl. No.: 14/767,880

(22) PCT Filed: Feb. 13, 2014

(86) PCT No.: PCT/JP2014/053317
§ 371 (c)(1),
(2) Date: Aug. 13, 2015

(87) PCT Pub. No.: WO2014/126146
PCT Pub. Date: Aug. 21, 2014

(65) Prior Publication Data
US 2015/0376568 A1 Dec. 31, 2015

(30) Foreign Application Priority Data
Feb. 14, 2013 (JP) .................................. 2013-026946
Nov. 1, 2013 (JP) .................................. 2013-228611

(51) Int. Cl.
*C12N 5/00* (2006.01)
*C07K 14/195* (2006.01)
*C12N 9/10* (2006.01)

(52) U.S. Cl.
CPC .......... *C12N 5/0081* (2013.01); *C07K 14/195* (2013.01); *C12N 9/1077* (2013.01); *C07K 2319/33* (2013.01); *C07K 2319/55* (2013.01); *C12Y 204/02036* (2013.01)

(58) Field of Classification Search
USPC ................................................. 435/325, 455
See application file for complete search history.

(56) References Cited

U.S. PATENT DOCUMENTS

2015/0111218 A1  4/2015 Tateno et al.

FOREIGN PATENT DOCUMENTS

JP  200595027 A  4/2005
WO  2013128914 A1  9/2013

OTHER PUBLICATIONS

Sulak (Structure, Jan. 13, 2010, vol. 18, p. 59-72).*
Tang (Nature Biotechnology, 2011, vol. 29, No. 9, p. 829-834).*
Tateno (J. Biol. Chem., 2011, vol. 286, No. 23, p. 20345-20353).*
Tateno (Stem Cell Translational Medicine, 2013, vol. 3, p. 265-273).*
Tateno (Stem Cell Reports, May 2015, vol. 4, p. 811-820).*
Ben-David (Nature Comm., 2013, vol. 4, No. 1992, p. 1-8).*
Adler (JACC Cariovasc Imaging, 2009, vol. 2, No. 9, p. 1114-1122.*
Tateno, et al., Glycome Diagnosis of Human Induced Pluripotent Stem Cells Using Lectin Microarray; Journal of Biological Chemistry, Jun. 10, 2011, vol. 286, No. 23, pp. 20345-20353.
Tang, et al., An Antibody against SSEA-5 glycan on human pluripotent stem cells enables removal of teratoma-forming cells; Nature Biotechnology, Sep. 2011, vol. 29, No. 9, pp. 829-834 and "On-line Methods" page.
Sulak, et al., A TNF-like Trimeric Lectin Domain from Burkholderia cenocepacia with Specificity for Fucosylated Human Histo-Blood Group Antigens; Structure, Jan. 13, 2010, vol. 18, pp. 59-72.
Adewumi, et al., Characterization of human embryonic stem cell lines by the International Stem Cell Initiative; Jul. 2007, vol. 25, No. 7, pp. 803-816.
Weldon, et al., A guide to taming a toxin—recombinant immunotoxins constructed from Pseudomonas exotoxin A for the treatment of cancer; The FEBS Journal; 2011, vol. 278, pp. 4683-4700.
Mancheno, et al., Laetiporus sulphureus Lectin and Aerolysin Protein Family; in Proteins: Membrane Binding and Pore Formation (Landes Bioscience, 2010), pp. 67-80.
Onuma, et al., rBC2LCN, a new probe for live cell imaging of human pluripotent stem cells; Biochemical and Biophysical Research Communications, 2013, vol. 431, pp. 524-529.
Tateno, Podocalyxin Is a Glycoprotein Ligand of the Human Pluripotent Stem Cell-Specific Probe rBC2LCN; Stem Cells Translational Medicine, 2013, vol. 2, pp. 265-273.
Rumbaut, et al., Differential Phototoxicity of Fluorescent Dye-Labeled Albumin Conjugates; Microcirculation, 1999, vol. 6, pp. 205-213.
Tateno, et al., Frontal affinity chromatography: sugar-protein interactions; Nature Protocols, 2007, vol. 2, No. 10, pp. 2529-2537.
Liang, et al., Switching of the core structures of glycosphingolipids from globo- and lacto- to ganglio-series upon human embryonic stem cell differentiation; Proceedings of the National Academy of Sciences USA, Dec. 28, 2010, vol. 107, No. 52, pp. 22564-22569.

(Continued)

*Primary Examiner* — Michael C Wilson
(74) *Attorney, Agent, or Firm* — Pearne & Gordon LLP

(57) ABSTRACT

An object of the present invention is to provide a method for introducing a target substance into undifferentiated cells, and a carrier therefor, whereby the target substance can be specifically introduced into the undifferentiated cells by contacting the undifferentiated cells with an rBC2LCN-target substance fusion product in which rBC2LCN lectin is fused to the target substance. Particularly, an rBC2LCN-toxin fusion product in which rBC2LCN lectin is fused to a toxin functioning in cells or its domain having the ability to kill cells functions as an agent for eliminating undifferentiated stem cells and can be administered into a medium after inducing the differentiation of the stem cells to reliably kill only the stem cells in an undifferentiated state.

5 Claims, 13 Drawing Sheets

(56) References Cited

OTHER PUBLICATIONS

Hasehira, et al., Structural and Quantitative Evidence for Dynamic Glycome Shift on Production of Induced Pluripotent Stem Cells; Molecular & Cellular Protearnics 11-12, 2012, pp. 1913-1923.

Tateno, et al., Precise evaluation of iPS cells with rapid glycan profiling technique; ASIT National Institute of Advanced Industrial Science and Technology; Jun. 22, 2011, pp. 1-4 (and English translation pp. 1-6).

International Search Report and Written Opinion issued in International PCT Application No. PCT/JP2014/053317; dated May 20, 2014.

Extended European Search Report dated Jul. 19, 2016 for EP 14751402.0.

Sulak Ondrej et al. "Burkholderia cenocepacia BC2L-C Is a Super Lectin with Dual Specificity and Proinfiammatory Activity," PLoS Pathogens, vol. 7, No. 9, e1002238, Sep. 2011, pp. 1-14.

* cited by examiner

```
                        SEQUENCE LISTING

<160> NUMBER OF SEQ ID NOS: 7

<210> SEQ ID NO 1
<211> LENGTH: 156
<212> TYPE: PRT
<213> ORGANISM: Burkholderia cepacia

<400> SEQUENCE: 1

Met Pro Leu Leu Ser Ala Ser Ile Val Ser Ala Pro Val Val Thr Ser
1               5                   10                  15

Glu Thr Tyr Val Asp Ile Pro Gly Leu Tyr Leu Asp Val Ala Lys Ala
            20                  25                  30

Gly Ile Arg Asp Gly Lys Leu Gln Val Ile Leu Asn Val Pro Thr Pro
        35                  40                  45

Tyr Ala Thr Gly Asn Asn Phe Pro Gly Ile Tyr Phe Ala Ile Ala Thr
    50                  55                  60

Asn Gln Gly Val Val Ala Asp Gly Cys Phe Thr Tyr Ser Ser Lys Val
65                  70                  75                  80

Pro Glu Ser Thr Gly Arg Met Pro Phe Thr Leu Val Ala Thr Ile Asp
                85                  90                  95

Val Gly Ser Gly Val Thr Phe Val Lys Gly Gln Trp Lys Ser Val Arg
            100                 105                 110

Gly Ser Ala Met His Ile Asp Ser Tyr Ala Ser Leu Ser Ala Ile Trp
        115                 120                 125

Gly Thr Ala Ala Pro Ser Ser Gln Gly Ser Gly Asn Gln Gly Ala Glu
    130                 135                 140

Thr Gly Gly Thr Gly Ala Gly Asn Ile Gly Gly Gly
145                 150                 155

<210> SEQ ID NO 2
<211> LENGTH: 227
<212> TYPE: PRT
<213> ORGANISM: Pseudomonas aeruginosa

<400> SEQUENCE: 2

Glu Phe Leu Gly Asp Gly Gly Asp Val Ser Phe Ser Thr Arg Gly Thr
1               5                   10                  15

Gln Asn Trp Thr Val Glu Arg Leu Leu Gln Ala His Arg Gln Leu Glu
            20                  25                  30

Glu Arg Gly Tyr Val Phe Val Gly Tyr His Gly Thr Phe Leu Glu Ala
        35                  40                  45
```

```
Ala Gln Ser Ile Val Phe Gly Val Arg Ala Arg Ser Gln Asp Leu
        50                  55                  60

Asp Ala Ile Trp Arg Gly Phe Tyr Ile Ala Gly Asp Pro Ala Leu Ala
65                  70                  75                  80

Tyr Gly Tyr Ala Gln Asp Gln Glu Pro Asp Ala Arg Gly Arg Ile Arg
                85                  90                  95

Asn Gly Ala Leu Leu Arg Val Tyr Val Pro Arg Ser Ser Leu Pro Gly
               100                 105                 110

Phe Tyr Arg Thr Ser Leu Thr Leu Ala Ala Pro Glu Ala Ala Gly Glu
               115                 120                 125

Val Glu Arg Leu Ile Gly His Pro Leu Pro Leu Arg Leu Asp Ala Ile
       130                 135                 140

Thr Gly Pro Glu Glu Glu Gly Gly Arg Leu Glu Thr Ile Leu Gly Trp
145                 150                 155                 160

Pro Leu Ala Glu Arg Thr Val Val Ile Pro Ser Ala Ile Pro Thr Asp
                165                 170                 175

Pro Arg Asn Val Gly Gly Asp Leu Asp Pro Ser Ser Ile Pro Asp Lys
                180                 185                 190

Glu Gln Ala Ile Ser Ala Leu Pro Asp Tyr Ala Ser Gln Pro Gly Lys
            195                 200                 205

Pro Pro Arg Glu Asp Leu Lys Pro Pro His His His His His His Lys
        210                 215                 220

Asp Glu Leu
225

<210> SEQ ID NO 3
<211> LENGTH: 5
<212> TYPE: PRT
<213> ORGANISM: Artificial
<220> FEATURE:
<223> OTHER INFORMATION: spacer1

<400> SEQUENCE: 3

Gly Ser Gly Gly Gly
1               5

<210> SEQ ID NO 4
<211> LENGTH: 4
<212> TYPE: PRT
<213> ORGANISM: Artificial
<220> FEATURE:
<223> OTHER INFORMATION: spacer2

<400> SEQUENCE: 4

Gly Gly Gly Ser
1

<210> SEQ ID NO 5
<211> LENGTH: 396
<212> TYPE: PRT
<213> ORGANISM: Artificial
<220> FEATURE:
<223> OTHER INFORMATION: rBC2LCN-(GSGGG)2-ETA

<400> SEQUENCE: 5

Met Pro Leu Leu Ser Ala Ser Ile Val Ser Ala Pro Val Val Thr Ser
1               5                   10                  15

Glu Thr Tyr Val Asp Ile Pro Gly Leu Tyr Leu Asp Val Ala Lys Ala
            20                  25                  30
```

```
Gly Ile Arg Asp Gly Lys Leu Gln Val Ile Leu Asn Val Pro Thr Pro
            35                  40                  45

Tyr Ala Thr Gly Asn Asn Phe Pro Gly Ile Tyr Phe Ala Ile Ala Thr
 50                      55                  60

Asn Gln Gly Val Val Ala Asp Gly Cys Phe Thr Tyr Ser Ser Lys Val
 65                  70                  75                  80

Pro Glu Ser Thr Gly Arg Met Pro Phe Thr Leu Val Ala Thr Ile Asp
                85                  90                  95

Val Gly Ser Gly Val Thr Phe Val Lys Gly Gln Trp Lys Ser Val Arg
                100                 105                 110

Gly Ser Ala Met His Ile Asp Ser Tyr Ala Ser Leu Ser Ala Ile Trp
            115                 120                 125

Gly Thr Ala Ala Pro Ser Ser Gln Gly Ser Gly Asn Gln Gly Ala Glu
    130                 135                 140

Thr Gly Gly Thr Gly Ala Gly Asn Ile Gly Gly Ala Leu Glu Gly
145                 150                 155                 160

Ser Gly Gly Gly Ser Gly Gly Glu Phe Leu Gly Asp Gly Gly
                165                 170                 175

Asp Val Ser Phe Ser Thr Arg Gly Thr Gln Asn Trp Thr Val Glu Arg
            180                 185                 190

Leu Leu Gln Ala His Arg Gln Leu Glu Glu Arg Gly Tyr Val Phe Val
        195                 200                 205

Gly Tyr His Gly Thr Phe Leu Glu Ala Ala Gln Ser Ile Val Phe Gly
        210                 215                 220

Gly Val Arg Ala Arg Ser Gln Asp Leu Asp Ala Ile Trp Arg Gly Phe
225                 230                 235                 240

Tyr Ile Ala Gly Asp Pro Ala Leu Ala Tyr Gly Tyr Ala Gln Asp Gln
                245                 250                 255

Glu Pro Asp Ala Arg Gly Arg Ile Arg Asn Gly Ala Leu Leu Arg Val
                260                 265                 270

Tyr Val Pro Arg Ser Ser Leu Pro Gly Phe Tyr Arg Thr Ser Leu Thr
            275                 280                 285

Leu Ala Ala Pro Glu Ala Ala Gly Glu Val Glu Arg Leu Ile Gly His
    290                 295                 300

Pro Leu Pro Leu Arg Leu Asp Ala Ile Thr Gly Pro Glu Glu Glu Gly
305                 310                 315                 320

Gly Arg Leu Glu Thr Ile Leu Gly Trp Pro Leu Ala Glu Arg Thr Val
                325                 330                 335

Val Ile Pro Ser Ala Ile Pro Thr Asp Pro Arg Asn Val Gly Gly Asp
            340                 345                 350

Leu Asp Pro Ser Ser Ile Pro Asp Lys Glu Gln Ala Ile Ser Ala Leu
        355                 360                 365

Pro Asp Tyr Ala Ser Gln Pro Gly Lys Pro Pro Arg Glu Asp Leu Lys
    370                 375                 380

Pro Pro His His His His His Lys Asp Glu Leu
385                 390                 395

<210> SEQ ID NO 6
<211> LENGTH: 4
<212> TYPE: PRT
<213> ORGANISM: Artificial
<220> FEATURE:
<223> OTHER INFORMATION: ER retention signal

<400> SEQUENCE: 6
```

```
Lys Asp Glu Leu
1

<210> SEQ ID NO 7
<211> LENGTH: 8
<212> TYPE: PRT
<213> ORGANISM: Artificial
<220> FEATURE:
<223> OTHER INFORMATION: Nuclear localization signal iNLSj

<400> SEQUENCE: 7

Pro Pro Lys Lys Lys Arg Lys Val
1               5
```

METHOD OF INTRODUCING A TOXIN OR DYE INTO MAMMALIAN PLURIPOTENT CELLS USING RBC2LCN

TECHNICAL FIELD

The present invention relates to a method for eliminating stem cells responsible for tumorigenic transformation from a source of cells to be transplanted, and an agent for eliminating undifferentiated cells therefor. The method enables a highly safe cell source to be efficiently and conveniently provided, leading to the acceleration of regenerative medicine using stem cells.

The present invention also relates to a carrier for transport into undifferentiated cells and a composition for introduction into undifferentiated cells, which are capable of specifically introducing a target compound, such as a toxic compound, into the undifferentiated cells.

Pluripotent stem cells have attracted attention because of having the property of being capable of differentiating into all cells constituting the body and the property of being capable of maintaining their undifferentiated properties, and are not only applied to drug discovery screening and elucidation of disease mechanisms but also under world-wide study as a material for regenerative medicine.

The world's first phase 1 clinical trial using human ES cells started against acute spinal-cord injury in the U.S.A. in 2010; furthermore, an investigational new drug (IND) application for phase ½ clinical trials using human ES cells against retinal degenerative disease was approved by FDA; and regenerative medicine research using human pluripotent stem cells continues rapid development.

Particularly, iPS cells as new human pluripotent stem cells originating in Japan have great advantage that they have a low ethical roadblock because of, for example, no use of fertilized embryos and can be established also from autologous tissue, and thus they are receiving high expectations from the field of regenerative medicine. In Japan, Riken Center for Developmental Biology, Institute of Biomedical Research and Innovation Laboratory, and other institutes plan to start clinical studies using iPS cells with age-related macular degeneration patients as subjects in fiscal 2013, and Keio University also intends to start clinical studies in spinal cord injury patients in 2016.

As the clinical application of human pluripotent stem cells, such as ES cells and iPS cells, is started as just described above, a system to supply cells by securing quality and safety is not sufficiently developed.

Although pluripotent stem cells are not directly used but used after differentiating them into desired cells for transplantation in a cell therapy, it has been pointed out that if a source of cells having differentiated into desired cells is contaminated with undifferentiated stem cells, these undifferentiated stem cells become a cause of tumorgenesis. Accordingly, there is a need for the development of a technique for eliminating undifferentiated stem cells, i.e., tumorgenic cells from the cell source used for the cell therapy.

A method has conventionally been proposed, which involves incorporating the gene of a fluorescent protein, such as GFP, into downstream of the promoter of an undifferentiation-specific marker, such as Nanog, Oct3/4, or Stm1, and eliminating fluorescence-emitting undifferentiated cells by flow cytometry or the like (Patent Literature 1). However, this method consumes time and effort in modifying the genome and makes it difficult to treat a large amount of cells. Some previous reports have said that it is difficult to completely eliminate undifferentiated cells even by a method involving elimination by flow cytometry or the like using a single undifferentiated cell-specific antibody with which vital staining can be performed (Non Patent Literature 2). Accordingly, there has been a need for a method for reliably and efficiently eliminating only undifferentiated cells responsible for tumorigenic transformation from differentiated cells to be transplanted without damage the differentiated cells. Particularly, there has been a need for the development of an agent for conveniently and efficiently eliminating undifferentiated cells, as can kill only the undifferentiated cells simply by addition to a medium.

CITATION LIST

Patent Literature

Patent Literature 1: Japanese Patent Laid-Open No. 2005-95027

Non Patent Literature

Non Patent Literature 1: Tateno H, Toyota M, Saito S, Onuma Y, Ito Y, Hiemori K, Fukumura M, Matsushima A, Nakanishi M, Ohnuma K, Akutsu H, Umezawa A, Horimoto K, Hirabayashi J, Asashima M., J. Biol. Chem. 2011 Jun. 10; 286 (23): 20345-53.

Non Patent Literature 2: Tang C, Lee A S, Volkmer J P, Sahoo D, Nag D, Mosley A R, Inlay M A, Ardehali R, Chavez S L, Pera R R, Behr B, Wu J C, Weissman I L, Drukker M., Nat. Biotechnol. 2011 Aug. 14; 29 (9): 829-34.

Non Patent Literature 3: Sulak O, Cioci G, Delia M, Lahmann M, Varrot A, Imberty A, Wimmerova M., Structure 2010 Jan. 13; 18 (1): 59-72.

Non Patent Literature 4: International Stem Cell Initiative Nat. Biotechnol. 2007 July; 25 (7): 803-16.

Non Patent Literature 5: Weldon J E, Pastan I. FEBS J. 2011 December; 278 (23): 4683-700. Review.

Non Patent Literature 6: Mancheno J M, Tateno H, Sher D, Goldstein I J. Adv. Exp. Med. Biol. 2010; 677: 67-80. Review.

Non Patent Literature 7: Onuma, Y., et al, (2013) Biochem. Biophys. Res. Commun., 431, 524-529.

Non Patent Literature 8: Tateno H., et. al, (2013) Stem Cells Transl. Med. 2, 265-273.

Non Patent Literature 9: Rumbaut R E, Sial A J. Microcirculation 1999 September; 6 (3): 205-13.

Non Patent Literature 10: Tateno H, et. al, Nakamura-Tsuruta S, Hirabayashi J. Nat. Protoc. 2007; 2 (10): 2529-37.

Non Patent Literature 11: Liang Y J, et. al, Proc. Natl. Acad. Sci. USA. 2010 Dec. 28; 107 (52): 22564-9.

Non Patent Literature 12: Hasehira K, et. al, Stem Cells Transl. Med. 2013 April; 2 (4): 265-73.

SUMMARY OF INVENTION

Technical Problem

An object of the present invention is to provide a convenient and efficient method for eliminating undifferentiated cells from differentiated cells to be transplanted and, specifically, to provide a method for reliably eliminating only stem cells in an undifferentiated state using a fusion product in which a toxoprotein or its domain having the ability to kill cells, an RNAi substance, or a toxic compound (toxin)

having cytotoxicity, such as a toxic low molecular weight compound, is fused to a lectin capable of selectively reacting with only stem cells in an undifferentiated state, and an agent for eliminating undifferentiated cells therefor.

At the same time, an object of the invention is to provide a carrier for intracellular transport, for specifically transporting a target compound into the undifferentiated cells (an agent for introduction into cells).

Solution to Problem

Previously, the present applicants exhaustively analyzed the sugar chain profiles of human iPS cells (114 specimens) prepared from 5 types of different somatic cells (skin, fetal lung, endometrial membrane, placental artery, and amniotic membrane) and human ES cells (9 specimens), using lectin microarray. As a result, despite the different sugar chain profiles of the original somatic cells for each tissue, it was found that all of the prepared iPS cells showed almost the same sugar chain profile and the introduction of reprogramming genes caused uniform convergence into sugar chain structures analogous to those of ES cells. According to the results of analyzing the lectin array data of human ES/iPS cells and human somatic cells in detail, the expression level of α2-6Sia, α1-2Fuc, and type 1 LacNAc was presumed to be markedly increased in undifferentiated human ES/iPS cells compared to in somatic cells; thus, the presumption was further confirmed by a method using expression analysis of glycosyltransferase genes using DNA array (Non Patent Literature 1).

The rBC2LCN lectin used in the present invention is a recombinant obtained by expressing BC2LCN lectin (YP_002232818) corresponding to the N-terminal domain of BC2L-C protein derived from a gram-negative bacterium (*Burkholderia cenocepacia*), in transformed *Escherichia coli*, and is a lectin recognizing the sugars "Fucα1-2Galβ1-3GlcNAc" and "Fucα1-2Galβ1-3GalNAc" in the non-reducing terminus of a complex sugar chain (Non Patent Literatures 1 and 3).

In the above-described experiment using a lectin array, the present applicants found that the rBC2LCN lectin reacted with all human ES/iPS cells but completely failed to react with differentiated somatic cells. The lectin is construed to specifically react with the sugar chain structures "Fucα1-2Galβ1-3GlcNAc (=H type 1 structure)" and "Fucα1-2Galβ1-3GalNAc (=H type 3 structure)" having 2 (α1-2Fuc and type1 LacNAc) of "α1-2Fuc", "type1 LacNAc", and "α2-6Sia" as sugar chains highly expressed on human ES/iPS cells and hardly expressed on differentiated somatic cells.

This indicates that the sugar chain ligand recognized by the rBC2LCN lectin is a novel undifferentiation sugar chain marker characterizing undifferentiated stem cells and also indicates that the rBC2LCN lectin can be used as a probe specific for the undifferentiation sugar chain markers "Fucα1-2Galβ1-3GlcNAc" and/or "Fucα1-2Galβ1-3GalNAc" (hereinafter, both are sometimes together referred to as "Fucα1-2Galβ1-3GlcNAc/GalNAc").

Thereafter, the team of Drukker et al. found that an antibody recognizing "Fucα1-2Galβ1-3GlcNAc" recognized ES and iPS cells in an undifferentiated state (Non Patent Literature 2), supporting the above findings of the present applicants. However, the above antibody of Drukker et al. specifically reacts with "Fucα1-2Galβ1-3GlcNAc (=H type 1 structure)" but does not react with "Fucα1-2Galβ1-3GalNAc". This predicts that the antibody falls short of the rBC2LCN lectin from the viewpoint of discrimination when used to detect the undifferentiated stem cell markers because the antibody cannot detect "Fucα1-2Galβ1-3GalNAc" or "Fucα1-2Galβ1-3GalNAc-containing sugar chain" on undifferentiated stem cells as compared to the rBC2LCN lectin.

The present applicants have recently shown that whereas the rBC2LCN lectin very strongly stains human ES and iPS cells maintaining an undifferentiated state, the lectin completely fails to react with feeder cells or differentiated cells. The rBC2LCN lectin could be confirmed to by far surpass an antibody to a conventionally used undifferentiation marker (SSEA4, Tra-1-60, Tra-1-81, Nanog, or Oct3/4) in all performances envisioned in practical use, for example, the uniform, stable and highly reproducible ability to stain undifferentiated stem cells almost without observed background, binding to the cell surface marker with high sensitivity and high specificity, and the ability to stain undifferentiated stem cells alive in a state cultured in a medium without causing their undifferentiated properties to be lost or demonstrating toxicity, and has been applied for a patent (Japanese Patent Application No. 2012-267679, Non Patent Literature 7). The present applicants then identified podocalyxin as a target glycoprotein on the surface of undifferentiated stem cells, recognized by rBC2LCN (Non Patent Literature 12). Particularly, it was probable that rBC2LCN recognized an O-type sugar chain, especially "Fucα1-2Galβ1-3GalNAc (=H type 3 sugar chain)", on podocalyxin. Podocalyxin has a mucin-like domain; thus, the 0-type sugar chain recognized by rBC2LCN is predicted to form numerous clusters on podocalyxin (Non Patent Literature 8). The expression level of podocalyxin per se on undifferentiated cells is also high; thus, it follows that the target molecules recognized by rBC2LCN are present at high density on the undifferentiated cells. This result contributes to one of the reasons why rBC2LCN has the pronounced ability to specifically stain undifferentiated stem cells, exceptionally as a lectin.

It is expected that the use of the rBC2LCN lectin excellent in the specificity and affinity for undifferentiated cells enables the specific and efficient elimination of only undifferentiated stem cells responsible for tumorigenic transformation by treating a specimen containing undifferentiated cells with the lectin in the form of a fusion protein in which a toxin or its domain having the ability to kill cells is fused.

However, from the results of X-ray analysis of a binding state between the rBC2LCN lectin and a sugar chain previously reported, rBC2LCN is known to form a trimer and recognize the sugar chain in a state of putting the chain between 2 subunits (Non Patent Literature 3). This means that to maintain the natural "selectivity", "specificity", and "affinity" of the rBC2LCN lectin for undifferentiated stem cells when rBC2LCN is used in the form of a fusion protein, it is essential to retain the higher-order structure of its "trimer". As such, it was predicted to be extremely difficult for a fusion protein obtained by fusing rBC2LCN to a domain having the ability to kill cells to exert the natural function of killing cells, of the domain having the ability to kill cells while retaining the "trimer" structure of the rBC2LCN lectin and maintaining the "selectivity", "specificity", and "affinity" for undifferentiated stem cells. Not to mention, there was assumed to be almost no possibility of developing an rBC2LCN fusion protein combining such high selectivity, affinity, and killing ability as to be able to completely kill only undifferentiated cells simply by addition to the medium. In addition, when preparation from a soluble fraction of *Escherichia coli* was attempted in producing an rBC2LCN fusion protein, taking the size and higher order structure of the molecule of rBC2LCN per se into account, many difficulties were predicted in the construction of an efficient preparation method in a state in which the sugar chain binding activity of rBC2LCN was maintained.

As such many difficulties were predicted, the present applicants first focused attention on a domain having the ability to kill cells, of the type acting on the cell surface and having the function of forming pores on cells, as a candidate for a domain having the ability to kill cells, having a minimized effect on the higher order structure expected in rBC2LCN and capable of being expected to have a large cytocidal effect. Known domains having the ability to kill cells, of the type having the function of forming pores on cells include, for example, aerolysin (Non Patent Literature 6); among others, a fusion protein with a C-terminal domain of LSLa lectin (rBC2LCN-LSLC) was prepared (Non Patent Literature 6). LSLa lectin is a lectin derived from *Laetiporus sulphureus* as a type of mushroom and is known to recognize an N-acetyllactosamine sugar chain on the cell surface and be multimerized on the cell surface to perforate the cell membrane to kill the cells (Non Patent Literature 6). A fusion protein (rBC2LCN-LSLC) could be produced in transformed *Escherichia coli*, followed by purifying on the order of several hundred micrograms per one-litter culture from a soluble fraction of the *Escherichia coli*. However, a high-purity purified product could not be obtained, and the resultant had no multimer-forming ability or ability to kill undifferentiated cells; thus, it was probable that the steric structures of both domains had been broken. Accordingly, so as not to damage the steric structures of rBC2LCN and LSLC, a linker for providing a sufficient distance between both domains, in which Gly-Gly-Gly-Ser was repeated 1 to 3 times was introduced to prepare rBC2LCN-$(GGGS)_{1-3}$-LSLC. rBC2LCN-$(GGGS)_{1-3}$-LSLC were purified and then reacted at various concentrations with undifferentiated stem cells; however, none of the fusion proteins, unfortunately, had the ability to kill the undifferentiated cells.

In light of the results, it was concluded that a domain or toxin acting on the cell surface and having the ability to kill the cells could likely not sufficiently exercise the killing ability on undifferentiated cells; then, a cell-killing toxin was tried, which was of the type acting in the cells and had the activity of inhibiting the protein synthesis of the cells. Peptide binding was selected as a binding mode, and sufficient distance was provided between both domains. A domain region having the ability to kill cells, derived from exotoxin A (ETA) secreted by *Pseudomonas aeruginosa* (the region is hereinafter sometimes referred to as "ETA"), as a typical cell-killing toxin having the activity of inhibiting protein synthesis, was used as the toxoprotein to prepare a fusion protein in which the toxoprotein was bonded to rBC2LCN by peptide binding. In this regard, "rBC2LCN-$(GSGGG)_2$-ETA" was synthesized using the sequence in which Gly-Ser-Gly-Gly-Gly was repeated 2 times, as a linker to make an rBC2LCN-ETA fusion protein in which sufficient distance was provided between rBC2LCN and ETA. When the protein was expressed in transformed *Escherichia coli*, followed by applying its soluble fraction to affinity chromatography, "rBC2LCN-ETA" fusion protein could be purified in a homogeneous state by only a single operation.

When rBC2LCN was examined for multimer formation by gel filtration chromatography, it was found to form not the trimer previously reported in a paper but a dimer. Then when rBC2LCN-ETA was also examined, it was found to form a dimer, like wild-type rBC2LCN. This result was surprising because there was concern that conversion to the fusion protein disrupted the multimer-forming ability. On examination of the dissociation constant to H type 1/3 as a sugar chain ligand for rBC2LCN, the constant of rBC2LCN-ETA as a fusion protein (H type 1: 9.9 μM, H type 3: 32.3 μM) was found to be comparable to that of wild-type rBC2LCN (H type 1: 8.3 μM, H type 3: 25.4 μM). In addition, the binding property of the fusion protein to human iPS cells was found to be comparable to that of wild-type rBC2LCN. These results showed that rBC2LCN-ETA as a fusion protein had almost the same binding properties as those of wild-type rBC2LCN. The addition of rBC2LCN-ETA to a medium having human ES or iPS cells maintaining an undifferentiated state cultured could be confirmed to have the effect of killing human ES or iPS cells in the medium with high efficiency. In addition, the action was found to be an action retaining prominent specificity for undifferentiated cells completely without affecting feeder cells and differentiated cells present in the same medium. Then, continued culture for a long period of time under the same conditions was also confirmed not to change differentiated cell characteristics. These results mean that the rBC2LCN-ETA specifically bound to "Fucα1-2Galβ1-3GlcNAc/GalNAc" sugar chain on the undifferentiated cell surface and then rapidly entered the undifferentiated cells and the "ETA" domain acted in the undifferentiated cells, totally inhibited protein synthesis in the undifferentiated cells by ADP-ribosylating EF2 peptide elongation factor essential for the protein synthesis, and finally induced cell death. It was surprising and an unexpected piece of luck for the applicants that the undifferentiated cell-killing action of "rBC2LCN-ETA" was extremely strong.

Here, the fact that "rBC2LCN-ETA" exhibited a strong cell-killing action in undifferentiated cells means that the "rBC2LCN-ETA" fusion product has the ability to entry the undifferentiated cells because it is construed that the rapid entry of the fusion product of "rBC2LCN" and "ETA" into the undifferentiated cells enabled the sufficient exertion of the protein synthesis-inhibiting action of "ETA" in the cells. When a lectin recognizes a specific sugar chain on the cell surface, it is typically observed in a state specifically binding to the sugar chain on the cell surface, but the phenomenon of its entry into the cells through the recognized sugar chain is little known. Considering this, the phenomenon of the entry of "rBC2LCN" fused to ETA into the undifferentiated cells was unexpected, and it was probable that "rBC2LCN" had the possibility of having the action of specifically binding to the "Fucα1-2Galβ1-3GlcNAc/GalNAc" sugar chain on the undifferentiated cell surface as well as the action of causing entry into the undifferentiated cells through the sugar chain after binding, as the characteristic of "rBC2LCN".

Accordingly, a toxin certainly acting in cells was believed to be suitable as the toxin exerting the effect of killing undifferentiated cells by binding to "rBC2LCN", and was selected from toxins having the activity of inhibiting protein synthesis like ETA.

Known cell-killing toxins having the activity of inhibiting protein synthesis include highly poisonous lysin and saporin derived from plant seeds, and exotoxins derived from bacteria; among these, saporin was studied, which could be purchased as a fusion protein with streptavidin. Saporin is a proteinous toxin contained in the seed of *Saponaria officinalis*, a protein which can directly inactivate ribosomes to cause cell death at an extremely low concentration, and is commercially available as Streptavidin-ZAP in which streptavidin is fused (Advanced Targeting Systems).

rBC2LCN was biotinylated and then subjected to biotin-avidin binding to Streptavidin-ZAP to prepare rBC2LCN-ZAP, which was then reacted with undifferentiated stem cells. In the initial experiment, although the undifferentiated stem cells were exposed to the rBC2LCN-ZAP fusion product (streptavidin-fused saporin+biotinylated rBC2LCN) at the three stages of 1 ng, 10 ng, and 100 ng/2 ml in terms of a Streptavidin-ZAP concentration, no activity of killing the undifferentiated cells could be confirmed. Initially, the results were interpreted as due to that the sugar binding activity of rBC2LCN was greatly impaired because the fusion of the toxin to rBC2LCN using the biotin-avidin system led to the random binding of many toxin to each other; however, it was then noticed that the amount of rBC2LCN and the toxin used in the initial assay had the possibility of being insufficient as an amount for causing the activity of killing undifferentiated cells. Accordingly, when the rBC2LCN-ZAP fusion product was again caused to act at a concentration of 100 times or more the initial concentration on undifferentiated stem cells, only the undifferentiated stem cells could be killed. In other words, it could be confirmed that the type of the toxin in the rBC2LCN-toxin fusion product was not limited to ETA and even when the binding mode to rBC2LCN was not only covalent binding but also the streptavidin-biotin binding mode, an rBC2LCN-toxin fusion product substantially containing the toxin at a sufficient amount for killing could be caused act to efficiently kill undifferentiated stem cells.

In addition, the effect of killing undifferentiated stem cells when a low molecular weight toxin was conjugated to rBC2LCN was studied. The low molecular weight toxin used was FITC whose photocytotoxicity effect was known (Non Patent Literature 9). FITC-labeled rBC2LCN was added to a medium in which human iPS cells maintaining an undifferentiated state were cultured, and 1 hour later, excitation light was irradiated for longer than the typical irradiation time. As a result, it was found that not only the protein toxin but also the low molecular weight compound toxin could be applied since the effect of highly efficiently killing human iPS cells could be confirmed. FITC may be used for labeling a cell surface antigen; however, its property of entering cells is not reported, and the mechanism by which FITC causes photocytotoxicity is also unknown. In the present invention, an experimental result has been obtained, in which FITC in the FITC-rBC2LCN fusion product had no cytotoxicity on differentiated cells whose cell surface had no sugar chain recognized by rBC2LCN, thus, it is unlikely that the fusion of FITC resulted in "rBC2LCN" acquiring the ability to entry cells. This has strongly suggested that the ability of the FITC-rBC2LCN fusion product to enter cells is the natural characteristic of "rBC2LCN". Accordingly, "rBC2LCN" labeled with FITC or low toxicity Cy3 has been caused to act on undifferentiated cells, followed by observation according to time. As a result, it has been able to be confirmed that either toxin binds to a sugar chain on the undifferentiated cell surface in the beginning but is concentrated within cells with time.

The above results have been able to demonstrate that the wild-type "rBC2LCN" itself used in the present invention has the effects of not only recognizing, and binding to, the "Fucα1-2Galβ1-3GlcNAc/GalNAc" sugar chain on the undifferentiated cell surface but also entering the cells through the sugar chain or a complex carbohydrate in which the sugar chain binds. This means that when undifferentiated cells are to be specifically killed, any toxin as a toxin component having the ability to kill cells can rapidly enter the undifferentiated cells by binding to rBC2LCN and acting on the undifferentiated cells in the form of "rBC2LCN-toxin" fusion product and thus can exert the natural cytotoxicity of the toxin in the cells. Particularly, the selection of a toxin of the type capable of exerting cytotoxicity in cells as a toxin, e.g., a toxoprotein or a low molecular weight compound toxin having a protein synthesis-inhibiting action, enables the efficient exertion of the ability to kill cells in the undifferentiated cells.

In addition, according to the present invention, no change in the characteristics of differentiated cells has been observed even when the differentiated cells continue to be cultured for a long period of time in a state in which an rBC2LCN-toxin fusion protein is added to the medium; the fusion protein has been able to be confirmed to be not toxic at all to the differentiated cells and thus can be directly used as a cell transplantation material for regenerative medicine. In other words, the rBC2LCN-toxin fusion protein of the present invention can efficiently kill and eliminate remaining undifferentiated cells in a cell source in which human ES and iPS cells are differentiated, simply by being added to the medium, enabling a reduction in the risk of tumorigenic transformation of the cell transplantation material.

Recent research by the present applicants (Non Patent Literature 7) has confirmed that the continuation of the culture of undifferentiated cells in the presence of rBC2LCN over a long period does not affect their proliferative properties, i.e., that rBC2LCN itself has no toxicity to undifferentiated cells. When undifferentiated cells are now cultured for a long period of time in the presence of "Cy3-rBC2LCN" in which rBC2LCN is bound to Cy3 as a less toxic dye compound for labeling, the fusion product has been fluorescently observed to migrate through the undifferentiated cell surface into the cells with time. In other words, "Cy3" has been able to be confirmed to be conveyed to the cell interior of undifferentiated cells by rBC2LCN to be capable of exerting the natural function of the "Cy3" in the cells. For FITC as a dye compound for labeling, exerting toxicity after several tens of seconds of irradiation, only cell internalization has been able to be confirmed to be observed without killed undifferentiated cells if the irradiation is brief irradiation within several seconds for common fluorescent observation.

So viewed, it has been demonstrated that even a substance other than a toxin and a dye compound for labeling, such as a nucleic acid or a physiologically active protein, can be caused to act on undifferentiated cells by fusion to rBC2LCN to efficiently transport the substance into the undifferentiated cells without threatening the survival of the cells and can exert the natural function of the substance.

This means that rBC2LCN has functioned as a carrier (an agent for intracellular introduction) for transporting various compounds specifically into undifferentiated cells, and thus an intracellular transport system specific for the undifferentiated cells, using rBC2LCN as a carrier can also be said to have been able to be provided.

The present invention has been accomplished by obtaining the above findings.

Thus, the present invention encompasses the following inventions.

[1] A method for introducing a target substance into undifferentiated cells, comprising chemically or electrically fusing the target substance to rBC2LCN, and contacting the resultant rBC2LCN-target substance fusion product with the undifferentiated cells.

[2] The method for introduction into undifferentiated cells according to [1] above, wherein the target substance and rBC2LCN are covalently bound to each other through or not through a linker or a spacer.

[3] The method for introduction into undifferentiated cells according to [1] above, wherein the target substance and rBC2LCN are fused to each other by biotin-streptavidin binding through or not through a linker or a spacer.

[4] The method for introduction into undifferentiated cells according to any one of [1] to [3] above, wherein the rBC2LCN-target substance fusion product is labeled by a fluorescent substance or a luminescent enzyme, comprising a step of determining that the target substance has been taken up in the undifferentiated cells, by observing a position at which fluorescence or luminescence is emitted.

[5] A carrier for introducing a target substance into undifferentiated cells, comprising rBC2LCN as an active ingredient.

[6] The carrier for introduction into undifferentiated cells according to [5] above, wherein the carrier for introduction into undifferentiated cells is caused to enter the undifferentiated cells in the form of an rBC2LCN-target substance fusion product obtained by forming a chemical or electrical fusion product of the target substance with rBC2LCN comprised as an active ingredient.

[7] A composition for introducing a target substance into undifferentiated cells, comprising an rBC2LCN-target substance fusion product in which the target substance and rBC2LCN are chemically or electrically fused to each other, as an active ingredient.

[8] The composition for introduction into undifferentiated cells according to [7] above, wherein the rBC2LCN-target substance fusion product is labeled by a fluorescent substance or a luminescent enzyme.

[9] The composition for introduction into undifferentiated cells according to [7] or [8] above, wherein the target substance and rBC2LCN are covalently bound to each other through or not through a linker or a spacer.

[10] The composition for introduction into undifferentiated cells according to [9] above, wherein the target substance is a protein, the rBC2LCN-target substance fusion product in which the target substance and rBC2LCN are covalently bound to each other through or not through a linker or a spacer being an expression product obtained using a fused gene in which the respective genes are bound to each other.

[11] The composition for introduction into undifferentiated cells according to [7] or [8] above, wherein the target substance and rBC2LCN are fused to each other by biotin-streptavidin binding through or not through a linker or a spacer.

[12] The composition for introducing into undifferentiated cells according to any one of [7] to [11] above, wherein the target substance is a toxic compound capable of exerting cytotoxicity in cells.

[13] The composition for introduction into undifferentiated cells according to [12] above, wherein the toxic compound is a protein toxin or a domain thereof having the ability to kill cells, a low molecular weight compound having cytotoxicity, or a nucleic acid.

[14] The composition for introduction into undifferentiated cells according to [12] or [13] above, wherein the toxic compound and rBC2LCN are fused to each other by covalent binding or biotin-streptavidin binding through or not through a linker or a spacer.

[15] The composition for introduction into undifferentiated cells according to [14] above, wherein the toxic compound is a protein toxin, the composition being an rBC2LCN-protein toxin fusion product in which the toxin and rBC2LCN are covalently bound to each other through or not through a linker or a spacer.

[16] The composition for introduction into undifferentiated cells according to [15] above, wherein the rBC2LCN-protein toxin fusion product is an expression product obtained using a fused gene in which an rBC2LCN gene and a protein toxin gene are bound to each other through or not through a spacer sequence.

[17] The composition for introduction into undifferentiated cells according to [15] or [16] above, wherein the protein toxin is a killing domain derived from *Pseudomonas aeruginosa* Exotoxin A (ETA).

[18] The composition for introduction into undifferentiated cells according to [14] above, the composition being an rBC2LCN-protein toxin fusion product in which the toxic compound and rBC2LCN are fused to each other by biotin-streptavidin binding through or not through a linker or a spacer.

[19] The composition for introduction into undifferentiated cells according to [14] above, wherein the toxic compound is a toxic low molecular weight compound fusion product, the composition being an rBC2LCN-toxic low molecular weight compound in which rBC2LCN and the toxic low molecular weight compound are fused to each other through or not through a linker or a spacer.

[20] An agent for eliminating undifferentiated stem cells, comprising an rBC2LCN-toxic compound fusion product in which a toxic compound capable of exerting cytotoxicity in cells and rBC2LCN are chemically or electrically fused to each other, as an active ingredient.

[21] The agent for eliminating undifferentiated stem cells according to [20] above, wherein the toxic compound is a protein toxin or a domain thereof having the ability to kill cells, a low molecular weight compound having cytotoxicity, or a nucleic acid.

[21] The agent for eliminating undifferentiated stem cells according to [20] or [21] above, wherein the toxic compound and rBC2LCN are fused to each other by covalent binding or biotin-streptavidin binding through or not through a linker or a spacer.

[22] The agent for eliminating undifferentiated stem cells according to [21] above, wherein the toxic compound is a protein toxin, the agent being an rBC2LCN-protein toxin fusion product in which the toxin and rBC2LCN are covalently bound to each other through or not through a linker or a spacer.

[23] The agent for eliminating undifferentiated stem cells according to [22] above, wherein the rBC2LCN-protein toxin fusion product is an expression product obtained using a fused gene in which an rBC2LCN gene and a protein toxin gene are bound to each other through or not through a spacer sequence.

[24] The agent for eliminating undifferentiated stem cells according to [22] or [23] above, wherein the protein toxin is a killing domain derived from *Pseudomonas aeruginosa* Exotoxin A (ETA).

[25] The agent for eliminating undifferentiated stem cells according to [21] above, the agent being an rBC2LCN-protein toxin fusion product in which the toxic compound and rBC2LCN are fused to each other by biotin-streptavidin binding through or not through a linker or a spacer.

[26] The agent for eliminating undifferentiated stem cells according to [21] above, wherein the toxic compound is a toxic low molecular weight compound, the agent being an rBC2LCN-toxic low molecular weight compound fusion product in which rBC2LCN and the toxic low molecular weight compound are fused to each other through or not through a linker or a spacer.

[27] A method for killing stem cells in an undifferentiated state, comprising adding rBC2LCN and the agent for eliminating undifferentiated stem cells according to any one of [20] to [26] above capable of exerting cytotoxicity to a medium after inducing stem cell differentiation.

[28] A method for producing a transplantation material for regeneration medicine, comprising a step of contacting differentiation-induced cells from stem cells with the agent for eliminating undifferentiated stem cells according to any one of [20] to [26] above.

[29] The production method according to [28] above, comprising culturing the stem cells on a beads-shaped, hollow fiber shaped, or plate-shaped substrate, subjecting the cells to differentiation induction treatment, and then adding the agent for eliminating undifferentiated stem cells to a medium in which the substrate is present.

[30] The production method according to [28] above, subjecting the stem cells to floating culture in a culture medium, subjecting the cells to differentiation induction treatment, and then adding the agent for eliminating undifferentiated stem cells to a culture medium in which a substrate is present.

Advantageous Effect of Invention

The present invention has first found that rBC2LCN functions as a carrier for specifically transporting various substances into undifferentiated cells (an agent for intracellular introduction), enabling the provision of an intracellular transport system specific for the undifferentiated cells.

When the composition comprising a fusion product of rBC2LCN and any of various target substances provided by the present invention is caused to act on a cell group in which undifferentiated cells are present, it can specifically enter the undifferentiated cells and efficiently transport the target substance into the undifferentiated cells for the exertion of the natural function of the target substance in the undifferentiated cells; thus, the composition can be said to be "composition for introduction into undifferentiated cells" for the target substance.

For example, the rBC2LCN-toxin fusion product provides excellent "agent for eliminating undifferentiated cells" capable of specifically killing undifferentiated stem cells simply by addition to a medium. Whereas the "agent for eliminating undifferentiated cells" of the present invention can be directly added to a medium for test cells to kill stem cells in an undifferentiated state, even long-term culture in the presence of the "agent for eliminating undifferentiated cells" is non-toxic to differentiated cells.

Thus, the "agent for eliminating undifferentiated cells" of the present invention can conveniently and efficiently eliminate human iPS/ES cells as tumorgenic cells from the cell source used for transplant, enabling the preparation of highly safe transplant cells; thus, the agent is expected to be applied to regenerative medicine using human ES/iPS cells.

Figure 1:
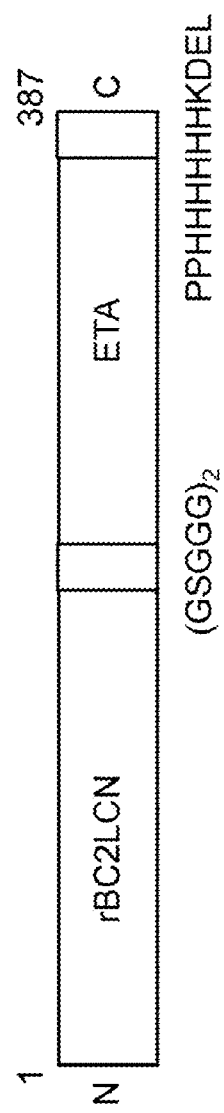
FIG. 1 is a schematic diagram showing a structure of an rBC2LCN-ETA subunit.

DESCRIPTION OF EMBODIMENTS 1. rBC2LCN Lectin (1-1) Ability of "rBC2LCN Lectin" to Recognize Sugar Chain The "rBC2LCN lectin" or its modified product used in the present invention specifically binds to "Fucα1-2Galβ1-3GlcNAc (formula 1)" and "Fucα1-2Galβ1-3GalNAc (formula 2)" as undifferentiation sugar chain markers on the cell surface.

The "BC2LCN lectin" is a lectin found from a gram-negative bacterium (Burkholderia cenocepacia) and corresponds to an N-terminal domain of a protein called BC2L-C (GenBank/NCBI-GI Accession No. YP_002232818) (Non Patent Literature 3). BC2LCN is known to show structural similarity to TNF-like protein, form a trimer in a solution, and recognize each sugar chain in a state of putting the chain between 2 subunits. Analysis using a sugar chain array has demonstrated that the lectin exhibits binding specificity to "Fucα1-2Galβ1-3GlcNAc (=H type 1 sugar chain)" and "Fucα1-2Galβ1-3GalNAc (=H type 3 sugar chain)" as well as "Lewis b sugar chain (Fucα1-2Galβ1-3(Fucα1-4)GlcNAc)" and "Globo H sugar chain (Fucα1-2Galβ1-3GalNAcβ1-3Galα1-4Galβ1-4Glc)" as sugar chain structures each containing the H type 1 sugar chain or the H type 3 sugar chain.

The "BC2LCN lectin" can also be bulk-produced by transformed bacteria because it contains no sugar chain. Specifically, BC2LCN gene encoding the amino acid sequence of GenBank/NCBI-GI Accession No. YP_002232818 (SEQ ID NO: 1) (Genome ID: 206562055) can be used, expressed in transformed Escherichia coli or the like after properly optimizing it for the host, and purified by a conventional protein purification means. An embodiment of the present invention also uses recombinant BC2LCN (rBC2LCN), which is hereinafter also referred to as "rBC2LCN".

In this regard, the BC2LCN lectin does not require the whole length corresponding to SEQ ID NO:1, and even if it is a sequence in which some amino acids are partially deleted, substituted, inserted, or added in SEQ ID NO: 1, it will do if it maintains the property of specifically recognizing the sugar chain structures represented by "Fucα1-

2Galβ1-3GlcNAc" and "Fucα1-2Galβ1-3GalNAc", i.e., "Fucα1-2Galβ1-3GlcNAc/GalNAc".

The rBC2LCN lectin or its modified product capable of being used as a carrier for the transport of a target substance into undifferentiated cells, including the "agent for eliminating undifferentiated cells" of the present invention can be expressed as follows.

The rBC2LCN or its modified product can be expressed as "a protein comprising the amino acid sequence shown in SEQ ID NO: 1 or an amino acid sequence in which one or several amino acids are deleted, substituted, inserted, or added in the shown amino acid sequence and specifically recognizing the sugar chain structures "Fucα1-2Galβ1-3GlcNAc" and "Fucα1-2Galβ1-3GalNAc".

Here, the "several" represents a natural number of 20 or less, preferably 10 or less, more preferably 5 or less. According to the present invention, the rBC2LCN lectin and its modified product are together simply referred to as "rBC2LCN".

(1-2) Ability of "rBC2LCN Lectin" to Enter Undifferentiated Cell

"rBC2LCN" used in the present invention has the characteristic of entering undifferentiated cells through "Fucα1-2Galβ1-3GlcNAc/GalNAc" as a recognition sugar chain or a protein or lipid bound to the sugar chain. Because "rBC2LCN" itself has no cytotoxicity, its characteristic of entry can be used to efficiently transport any of various compounds represented by various proteins and low molecular weight compounds (the compound to be transported is sometimes referred to as "target compound") into undifferentiated cells by fusing the compound to "rBC2LCN" and causing the resultant to act on the undifferentiated cells; the natural function of the transported compound can be exerted in the cells. If the transported compound is a compound capable of exerting toxicity in cells, it can exert its cytotoxicity.

The detailed entry mechanism is unknown, such as a route through which the fusion product of "rBC2LCN" and any of various compounds enters undifferentiated cells after binding to "Fucα1-2Galβ1-3GlcNAc/GalNAc" as the sugar chain that "rBC2LCN" recognizes. Podocalyxin modified by a complex sugar chain containing "Fucα1-2Galβ1-3GalNAc (=H type 3 sugar chain)" forms numerous clusters on the surface of undifferentiated cells, particularly ES or iPS cells having totipotency (Non Patent Literature 8); considering this, there is a possibility of entry through podocalyxin present on the undifferentiated cell surface, and to enable "rBC2LCN" to exert the ability to enter the undifferentiated cells, it is also possible that the cluster structure formed by podocalyxin is necessary. However, a Globo H-containing glycolipid containing the sugar chain in the constituent sugar has also been confirmed to be present specifically on the undifferentiated cell surface (Non Patent Literature 11), and the Globo H-containing glycolipid has the possibility of being present so as to cover the whole cell surface; thus, there is no denying that the fusion product could enter undifferentiated cells through the glycolipid.

Anyhow, the surface of undifferentiated cells, especially iPS/ES cells as pluripotent stem cells, is covered by many "Fucα1-2Galβ1-3GlcNAc/GalNAc" sugar chain-containing complex carbohydrates absent on the surface of differentiated cells, and "rBC2LCN" having formed a fusion product with any of various compounds is certain to have the ability to bind to the "Fucα1-2Galβ1-3GlcNAc/GalNAc" sugar chain on the undifferentiated cell surface and then enter the undifferentiated cells through the sugar chain or through the sugar chain-containing complex carbohydrates.

In other words, "rBC2LCN" can be said to be "carrier for intracellular transport (agent for intracellular introduction)" having "action of transport into cells" specific for undifferentiated cells, which transports any of various fused compounds (a target compound) into only the undifferentiated cells having the "Fucα1-2Galβ1-3GlcNAc/GalNAc"-containing complex carbohydrates on the cell surface.

According to the present invention, a fusion product in a form of a target substance to be transported chemically or electrically fused to rBC2LCN providing "carrier for intracellular transport" for undifferentiated cells according to the present invention and for introduction into undifferentiated cells is sometimes expressed simply as "rBC2LCN fusion product".

Then, the selection of a toxoprotein or a toxic low molecular weight compound capable of exerting cytotoxicity in cells as a compound to be fused enables the exertion of cytotoxicity only in undifferentiated cells and the specific killing of only the undifferentiated cells without affecting differentiated normal cells.

According to the present invention, the term "toxic compound" or "toxin" is used as a generic term applied to substances exerting toxicity to cells, including toxoproteins or toxic low molecular weight compounds, and cytotoxic nucleic acids, such as an RNAi substance, an antisense nucleic acid, and a ribozyme. The toxoprotein indicates a protein, a glycoprotein, a peptide, or the like which has cytotoxicity, and the term "toxic low molecular weight compound" includes all toxic compounds other than toxoproteins and nucleic acids, such as antibiotics and dyes. In the present invention, it is preferable to use a toxic compound capable of exerting cytotoxicity in the interior of cells, among the "toxic compounds".

Here, among undifferentiated cells, somatic stem cells, such as mesenchymal stem cells, have a small total amount of the "Fucα1-2Galβ1-3GlcNAc/GalNAc" sugar chain present on the cell surface compared to that for iPS/ES cells; thus, for a substance producing a positive effect on the undifferentiated cells, such as a physiologically active substance and a nutritive substance, just having to be able to be delivered even in a trace amount, the agent for intracellular introduction is effective as is the case with iPS/ES cells. However, for a fusion product with a toxin required to completely kill cells, the small total amount of the "Fucα1-2Galβ1-3GlcNAc/GalNAc" sugar chain essential for the recognition of rBC2LCN and its transport into cells on the cell surface decreases the amount of the toxin capable of being transported into the cells, results in less damage on the cells, and thus makes a reliable killing effect not possible. Thus, the cells of interest when the "rBC2LCN-toxin" fusion product of the present invention is used as an agent for eliminating undifferentiated cells are preferably stem cells having high totipotency, such as iPS/ES cells.

2. Compound to be Fused to rBC2LCN (Target Compound)

"rBC2LCN" can transport any type of compound desired to be transported into undifferentiated cells in a form fused to the compound into the cells by "action of transport into cells" specific for the undifferentiated cells. Specific Examples of the compound include proteins or glycoproteins such as toxoproteins, labeled proteins, and physiologically active proteins; lipids or glycolipids; nucleic acids such as DNA and RNA; dyes for labeling such as fluorescein derivatives; and other low molecular weight compounds. The fusion method here may be a genetically engineering binding method or a chemical binding method, as described later.

When cytotoxicity is attempted to be exerted in undifferentiated cells using "rBC2LCN-toxin fusion product" in which a toxin is bound to "rBC2LCN" of the present invention, any toxin can be fused for transport into the undifferentiated cells. However, the type of toxin extracellularly exerting cytotoxicity, such as the type of toxin destroying the cell wall, is inappropriate because the transport of the toxin into the cells does not enables the exertion of its natural cytotoxicity. Thus, the toxin to be fused to rBC2LCN according to the present invention is preferably a toxin capable of exerting a cytotoxic/cell-killing function in cells, particularly a protein toxin having a protein synthesis-inhibiting action in cells, a nucleic acid, such as an RNAi substance, or a low molecular weight compound toxin. A toxin having a protein synthesis-inhibiting action generally has a specific receptor on the cell surface; thus, the use of a wild-type full-length toxoprotein has the possibility of indiscriminately exerting cytotoxicity even in the form of a fusion product with rBC2LCN and therefore its cytotoxicity on differentiated cells is not negligible. In other words, when the "rBC2LCN-toxin" fusion product is used in vivo as an agent for eliminating undifferentiated cells, it is preferable to make a device eliminating the binding to the specific receptor on the cell surface, such as deleting a receptor-binding domain from the toxoprotein in advance or introducing mutation into the protein particularly because the fusion product is predicted to have great side effects. Such modification methods are well known to those skilled in the art. For example, for a *Pseudomonas aeruginosa* toxin (PE) as an exotoxin produced by *Pseudomonas aeruginosa*, modified PE is known, in which domain I region having a binding site to PE receptor and having the activity of binding to normal cells is eliminated at the gene level (Kondo, T., et al, J. Biol. Chem., 263, 9470-9475 (1988)). For a toxin derived from Exotoxin A of *Pseudomonas aeruginosa* (ETA) used in Examples of the present invention, only a cell-killing domain region (SEQ ID NO. 2) of the Exotoxin A of *Pseudomonas aeruginosa* is used.

The nucleotide sequence and amino acid sequence of each of various compounds to be fused to "rBC2LCN" used in the present invention, for example, various toxoproteins, can be obtained from commercial data bases. Specific examples thereof include diphtheria toxin (PDB Accession No. 1MDT), lysin (PDB Accession No. 2AAI), saporin (PDB Accession No. 3HIS), cholera toxin (PDB Accession No. 1XTC), enterotoxin (PDB Accession No. 1LTH), pertussigen (PDB Accession No. 1PRT) in addition to exotoxin A as an exotoxin of *Pseudomonas aeruginosa* (PDB Accession No. 1XK9). The compound does not have to be a full-length toxoprotein, but may contain a domain region having the ability to kill cells. For a non-protein toxin, a toxin compound capable of binding to a linker or a spacer can be similarly used.

For example, a gene encoding the amino acid sequence (SEQ ID NO: 2) corresponding to a domain region having a killing ability ("ETA"), of *Pseudomonas aeruginosa* exotoxin A (PDB Accession No. 1XK9) can be properly used in a host, such as *Escherichia coli*, by optimization for the host to produce the domain on a large scale from the transformed host.

*Pseudomonas aeruginosa* is a type of eubacterium belonging to Gram-negative aerobic rods. A typical exotoxin secreted by *Pseudomonas aeruginosa* is exotoxin A, which irreversibly inhibits any protein synthesis in animal cells by ADP-ribosylating EF2 as a peptide elongation factor, and thus finally leads to cell death.

3. Method for Binding Between rBC2LCN and Target Substance to be Transported

A case where a toxoprotein typical as a substance to be transported into undifferentiated cells is bound to rBC2LCN will be mainly described below in detail. However, the substance is not intended to be limited only to the toxoprotein.

(3-1) Fusion Method

A chemical method and a method for conjugation at the gene level are present as methods for fusion between rBC2LCN and a target substance to be transported into undifferentiated cells; the chemical method includes biotin-streptavidin binding in addition to covalent binding. A low molecular weight compound, such as FITC, can be randomly bound to a functional group (a hydroxyl group, an amino group, or the like) on the surface of rBC2LCN in a binding mode, such as covalent binding or hydrogen bonding by conventional chemical reaction to form an rBC2LCN fusion product.

For example, the method for fusion between "rBC2LCN" and "toxin" is preferably conversion to a fusion product by covalent binding, which can be performed by a chemical binding method using a divalent crosslinking agent or the like as a common method, inclusive of the case of the low molecular weight compound; the binding of an RNAi substance, such as siRNA, uses biotin-streptavidin binding, a fusion protein of rBC2LCN and a positively charged DNA-binding peptide (e.g., an Arg-rich cluster sequence derived from protamine; Winkler J, et al, Mol. Cancer Ther. 2009 September; 8 (9): 2674-83), or the like.

A nucleic acid such as RNAi generally assumes a negative charge; thus, to avoid direct contact with the similarly negatively charged surface of undifferentiated cells, it is preferable to make a device, such as forming a complex between the nucleic acid and a fusion protein consisting of rBC2LCN and a positively charged DNA-binding peptide in advance.

When the toxin is a protein toxin, binding is preferably performed at the gene level; here, both genes can be conjugated directly or using a common DNA linker by a well-known method.

It has first been shown according to the present invention that the conversion of rBC2LCN and a toxin to a fusion protein through a spacer sequence does not change the multimer-forming ability of rBC2LCN and its binding properties. The toxin fusion protein in which binding is performed at the gene level can be prepared as a homogeneous protein with no lot-to-lot difference and thus is particularly expected as an agent for eliminating undifferentiated stem cells, capable of being stably supplied. As a conjugation method, a method can also be used, which involves conjugating a toxin to rBC2LCN afterwards using a biotin-streptavidin system or the like; however, the method is labor-intensive and further has the problem of producing a lot-to-lot difference and making preparation as a homogeneous protein difficult because the toxin is randomly introduced into rBC2LCN. Thus, for chemical binding, it is also preferable to form a fusion product of rBC2LCN and a toxin by covalent binding, as in the case with the toxin fusion protein in which binding is performed at the gene level.

As a non-limiting example, the case where a typical protein toxin is covalently bound to rBC2LCN will be mainly described below in detail.

(3-2) Liker or Spacer

According to the present invention, a linker (crosslinker) or a spacer (spacer sequence) may be used in fusing rBC2LCN to a compound desired to be caused to act by transport into cells. To maximally exert the natural undifferentiated cell-specific binding and entry functions of "rBC2LCN" and the natural function of a compound to be transported, it is preferable to keep a certain distance between both of them; thus, binding is preferably performed through a linker/spacer having a suitable length. The linker/spacer having a suitable length is well known to those skilled in the art and can be synthesized as needed, and various ones are commercially available.

The spacer sequence for peptide binding used in the present invention is a well-known spacer consisting of an amino acid sequence of 4 to 10 amino acid residues capable of peptide binding and is used as a 1 to 3 times repeated sequence. Typically, an amino acid sequence consisting of glycine and/or serine, such as "GSGGG (SEQ ID NO: 3)" or "GGGS (SEQ ID NO: 4)", not forming a higher order structure is preferably used. For example, in transporting a toxoprotein into undifferentiated cells, rBC2LCN and a toxin capable of fusing to it or a domain of the toxin, having the ability to kill cells can be peptide-bound through each of the spacer sequences to keep a sufficient distance between both of them, enabling the maximal exertion of their respective abilities to bind to a sugar chain and kill the cells.

The above peptide linkers may also each be used in conjugation through chemical binding according to the present invention; preferred linkers include polyethylene glycol, particularly preferably a thiol linker having a thiol group introduced, capable of be cleaved with a reducing agent.

To bind a low molecular weight compound, a chemical binding agent, such as a divalent crosslinking agent, is often used; thus, it follows that rBC2LCN and a target substance are conjugated to each other using a linker derived from the binding agent.

When the rBC2LCN of the present invention is used for introducing a nucleic acid, such as an RNAi substance (e.g., siRNA or miRNA) or various mRNA or DNA, into cells, it is commonly not the nucleic acid but a positively charged nucleic acid carrier, such as a DNA-binding peptide that is directly bound to rBC2LCN; however, a linker/spacer is sometimes used as needed to keep a suitable distance between rBC2LCN and the nucleic acid carrier.

In forming a fusion product, the side of a compound to be transported (target substance) can be bound to a signal for transport to an intracellular organelle to which the compound is desired to be transported, in cells to further efficiently guide it to the desired organelle (e.g., "KDEL sequence (SEQ ID NO: 6)" corresponding to a C-terminal endoplasmic reticulum retention signal in FIG. 1). When it is necessary to transport a substance to be transported, such as an RNAi substance, into the nucleus, the use of a nuclear translocation signal, such as "PPKKKRKV (SEQ ID NO: 7)" is effective.

Although unnecessary when a compound to be transported can sufficiently exert its function in the form of a fusion product with rBC2LCN, a cleavage site for intracellular protease can be inserted in advance when the compound is desired to be separated at the destination of transport, to properly separate the compound transported as a fusion product in cells. The method for introducing the cleavage site is well known to those skilled in the art. For example, if a basic amino acid target sequence (canonically, Arg-X-(Arg/Lys)-Arg) is inserted in advance, it is cleaved by a $Ca^{2+}$-dependent transmembrane serine endoprotease called furin (Weldon J E, et al., FEBS J. 2011 December; 278 (23): 4683-700.). When a nucleic acid, such as DNA or an RNAi substance, is introduced into undifferentiated cells, it is rapidly separated after arrival into the cells in the form of a complex formed by a charge-charge interaction with a positively charged substance, such as an Arg cluster, bound to rBC2LCN.

(3-3) Method for Producing Toxin-Fusion rBC2LCN Protein

The gene of a toxin, such as ETA, is introduced 5'- or 3'-terminal to BC2LCN gene in a BC2LCN-containing expression vector, if necessary, through a spacer to construct a toxin-fusion rBC2LCN protein expression vector. Next, the expression vector is transformed into competent cells. Then, the transformed host cells, such as *Escherichia coli*, are liquid-cultured by an ordinary method to induce the expression of the toxin-fusion rBC2LCN protein.

(3-4) Purification Method and Identification Method for Toxin-Fusion rBC2LCN Protein The toxin-fusion rBC2LCN protein expression-induced in *Escherichia coli* can be purified by applying a conventional protein purification method; and, preferably, it is provided to a fucose-immobilized column and purified by affinity chromatography. The purification degree of the resultant toxin-fusion rBC2LCN protein can be confirmed by electrophoresis, gel filtration, or the like.

4. "Carrier for Intracellular Transport (Agent for Intracellular Introduction)" for Undifferentiated Cell According to Present Invention (4-1) Undifferentiated Stem Cell into which Target Substance is to be Transported According to Present Invention As used herein, the undifferentiated stem cells into which the transport is to be performed mean pluripotent stem cells in an undifferentiated state, having a large amount of a "Fucα1-2Galβ1-3GlcNAc/GalNAc"-containing complex carbohydrate almost absent on differentiated cell surface, on the surface. Specific examples thereof include various somatic stem cells, such as hematopoietic stem cells, neural stem cells, and skin tissue stem cells, in addition to embryo-stem cells (ES cells) and stem cells obtained by dedifferentiating somatic cells by introducing a stem cell-specific expression gene or the like (iPS cells or the like). Particularly, ES cells or iPS cells having totipotency are in a state in which the cell surface is closely covered by the "Fucα1-2Galβ1-3GlcNAc/GalNAc"-containing complex carbohydrate recognized by rBC2LCN, enabling the full exertion of an intracellular transport effect by rBC2LCN as the carrier for intracellular transport according to the present invention through the sugar chain-containing complex lipid.

Stem cells, including ES cells, are probably controlled by a common mechanism in a substantial proportion of mammals as well as humans; thus, the stem cells of interest according to the present invention hold true also for the case of using stem cells derived from mammals other than humans, such as monkey, pig, cow, goat, sheep, mouse, and rat.

(4-2) Undifferentiated Stem Cell to be Killed by "Agent for Eliminating Undifferentiated Cell" of Present Invention The typical case where undifferentiated stem cells are attempted to be killed by the "agent for eliminating undifferentiated cells" of the present invention is a case where contaminating stem cells in an undifferentiated state are attempted to be completely eliminated in having induced the differentiation of stem cells to be specifically differentiated into various tissues. Thus, the effect of killing undifferentiated cells here not only just has to be able to result in transport into the cells but also is required to be able to result in the transport of a sufficient amount of a cytotoxic component able to reliably kill the cells into the cells.

So viewed, an rBC2LCN-toxin fusion product as the agent is most effective on ES/iPS cells as totipotent stem cells, having been confirmed to be in a state for the cell surface to be closely covered by the "Fucα1-2Galβ1-3GlcNAc/GalNAc"-containing complex carbohydrate recognized by rBC2LCN among undifferentiated stem cells, and thus can be expected to have a sufficient killing effect on the stem cells even at a small dose.

However, the lectin array analysis previously performed by the present applicants (Non Patent Literature 1) confirmed that whereas the "Fucα1-2Galβ1-3GlcNAc/GalNAc" sugar chain was almost completely absent on the cell surface on differentiated cells, such as fibroblasts, a certain amount of the sugar chain was undoubtedly present on somatic stem cells, such as hematopoietic stem cells and neural stem cells. Since an rBC2LCN-toxin fusion product has no toxicity on differentiated cells, the rBC2LCN-toxin fusion product can be administered in such a large amount that it can kill somatic stem cells; thus, the fusion product can also be expected to act as the "agent for eliminating undifferentiated cells" on somatic stem cells.

5. Method for Using "rBC2LCN Fusion Product" of Present Invention

The "rBC2LCN fusion product" or the "composition for introduction into undifferentiated cells" further containing a well-known pharmacologically acceptable carrier, a buffer, and the like according to the present invention can be applied to a system containing undifferentiated cells (cultured cell line or in vivo tissue) to specifically transport a target substance into undifferentiated cells. The most typical example is a case where a toxic compound is specifically transported into undifferentiated cells, i.e., a case where the "composition for introduction into undifferentiated cells" containing the "rBC2LCN fusion product" is used as the "agent for eliminating undifferentiated cells". Thus, the "agent for eliminating undifferentiated cells" will be described below without limitation thereto. The following method can also be properly modified and applied to the "composition for introduction into undifferentiated cells" when another target substance is transported.

<Method for Treating Differentiated Cells Containing Undifferentiated Cells Using "Agent for Eliminating Undifferentiated Cell" of Present Invention>

(5-1) Application to Differentiated Cells Adhering to Substrate

The "agent for eliminating undifferentiated cells" of the present invention can be applied to a case where contaminating undifferentiated cells are eliminated from differentiation-induced cells cultured on a beads-shaped, hollow fiber shaped, or plate-shaped substrate.

In this case, an agent for eliminating undifferentiated cells is added at a final concentration of on the order of 10 to 100 µg/ml to a solution in which the substrate is found to be present, at the timing at which desired cells have finished differentiation, followed by additional culture for 24 to 48 hours (However, the specific administration concentration is only an example when the agent is applied to ES/iPS cells as typical undifferentiated cells, and can be properly increased according to the total amount of the "Fucα1-2Galβ1-3GlcNAc/GalNAc" sugar chain on the surface of stem cells of interest.).

Then, if the possibility that the undifferentiated cells still remain is present by a method based on methods for detecting undifferentiated cells, as patent-applied for by the present applicants (Japanese Patent Application No. 2011-239919, PCT/JP2012/006983, and Japanese Patent Application No. 2012-267679), the agent for eliminating undifferentiated cells can also be newly added. As used herein, the "solution" may be a culture medium, or a buffer, a physiological saline, or the like after eliminating medium components. The agent binds to a sugar chain specifically expressed on undifferentiated cell surface, is taken up in the cells, and kills the cells.

Such an elimination-treated cell sample can be evaluated to be a cell group consisting of only differentiated cells not any longer contaminated with undifferentiated cells; thus, the same differentiation induction treatment can be performed to rapidly obtain differentiated cells having no risk of contamination with undifferentiated cells in large quantity.

Here, the method for "differentiation induction" of stem cells into neuronal cells, digestive system cells, or the like may be any method; for example, various known methods can be applied, including a method involving culturing stem cells in the presence of retinoic acid to differentiate them into neuronal cells and a method involving forming heart muscle cells from stem cells using a humoral factor, such as noggin. Because the expression level of the cell surface undifferentiation sugar chain marker of the present invention on the surface of differentiated cells is of a negligible extent, noise is expected to be extremely reduced even under differentiation induction conditions.

(5-2) Application to Differentiated Cell Suspended in Solution

The "agent for eliminating undifferentiated cells" of the present invention can be applied to a case where undifferentiated cells contaminated into differentiated cells in a solution are eliminated.

In this case, an agent for eliminating undifferentiated cells is added at a final concentration of on the order of 10 to 100 µg/ml to a solution at the timing at which desired cells have finished differentiation, followed by additional culture for 24 to 48 hours. Then, if the possibility that the undifferentiated cells still remain is found to be present by a method based on methods for detecting undifferentiated cells, as patent-applied for by the present applicants (WO2013/065302 and Japanese Patent Application No. 2012-267679), the agent for eliminating undifferentiated cells according to the present invention can also be newly added. As used herein, the "solution" may be a culture medium, or a buffer, a physiological saline, or the like after eliminating medium components.

The "agent for eliminating undifferentiated cells" of the present invention directly recognizes only stem cells in an undifferentiated state, is taken up in the cells, and kills the cells. In addition, if the possibility that a small number of the undifferentiated cells remain in the culture medium is present, labeled rBC2LCN can be added to the culture medium after treatment, followed by complete elimination using flow cytometry or the like.

(5-3) Preparation of Cell Transplantation Material for Regeneration Medicine

According to the present invention, desired differentiation-induced cells not contaminated with stem cells in an undifferentiated state can be obtained without damage. The differentiation-induced cells can be directly used as transplant cells for regeneration medicine simply by subculturing the treated cells several times or washing these cells several times with a buffer solution, such as PBS, to completely eliminate dead stem cells, feeder cells, and the like. For action on floating cells, dead stem cells can be eliminated by a method involving precipitation in a density gradient medium, or the like.

EXAMPLES

The present invention will be described below in detail with reference to Examples. However, the present invention is not intended to be limited thereto.

The terms and concepts according to the present invention are based on the meanings of the terms idiomatically used in the art, and various techniques used for practicing the present invention can be easily and positively performed by one of ordinary skill in the art based on known literature and the like, particularly except for the techniques whose written sources are acknowledged. Various analyses and the like have been performed in line with methods as described in the instruction manuals, catalogs, or the like of the analyzers, reagents, or kits used.

Reference shall be made as the contents of description of the present invention to the contents described in the art references, patent publications, and patent application specifications cited herein.

Example 1: Expression of Recombinant rBC2LCN-ETA in *Escherichia Coli*

The gene of the protein described in FIG. 1 was designed, incorporated into pET27b (Stratagene Co., Ltd.), and introduced into *Escherichia coli* strain BL21 Codon Plus (DE3)-RIL (Stratagene Co., Ltd., #230245). The transformant was suspended in 5 mL of LB culture medium containing 10 μg/mL kanamycin and cultured overnight. The precultured solution (5 mL) was added to 1 L of LB medium and cultured, and 2 to 3 hours later, 1 mL of 1 M IPTG (Fermentus Co., Ltd., #R-0392) was added to a final concentration of 1 mM when (OD600) reached around 0.4. After shake culture at 20° C. for 24 hours, bacterial cells were collected by centrifugation, suspended in a buffer, and subjected to ultrasonification, and the protein soluble fraction was extracted. The protein soluble fraction of *Escherichia coli* was subjected to affinity purification using a fucose sepharose column prepared by covalently binding commercial sepharose (from GE Healthcare Co., Ltd.) to fucose by the method of Matsumoto et al. (Matsumoto I, Mizuno Y, Seno N. (1979) J. Biochem. April; 85 (4): 1091-8.), and elution was performed using 0.2 M fucose.

Figure 2:
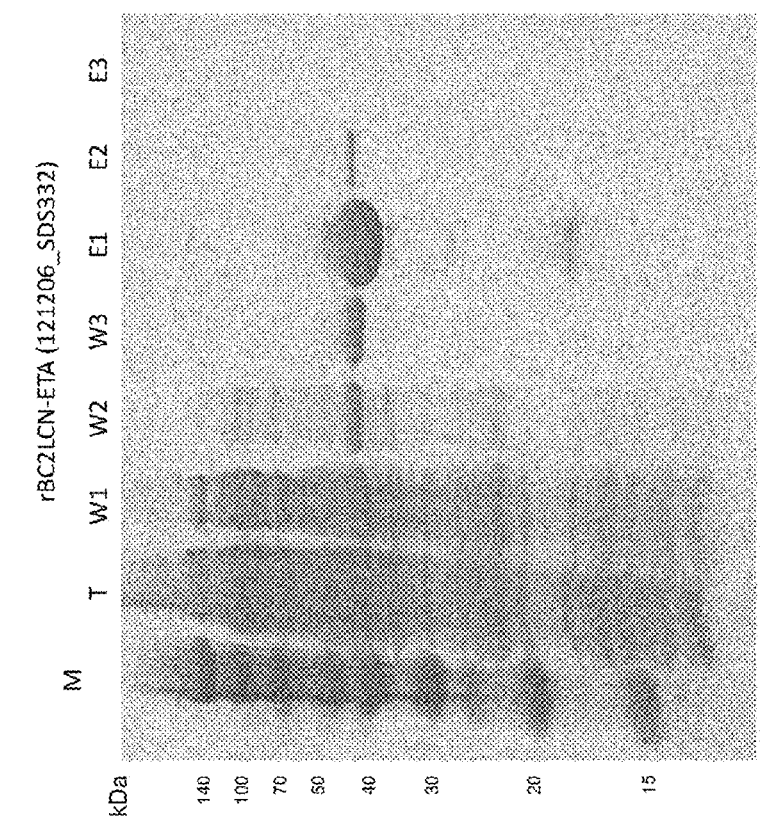
FIG. 2 is a photograph showing an electrophoretic profile during rBC2LCN-ETA purification.
Figure 3:
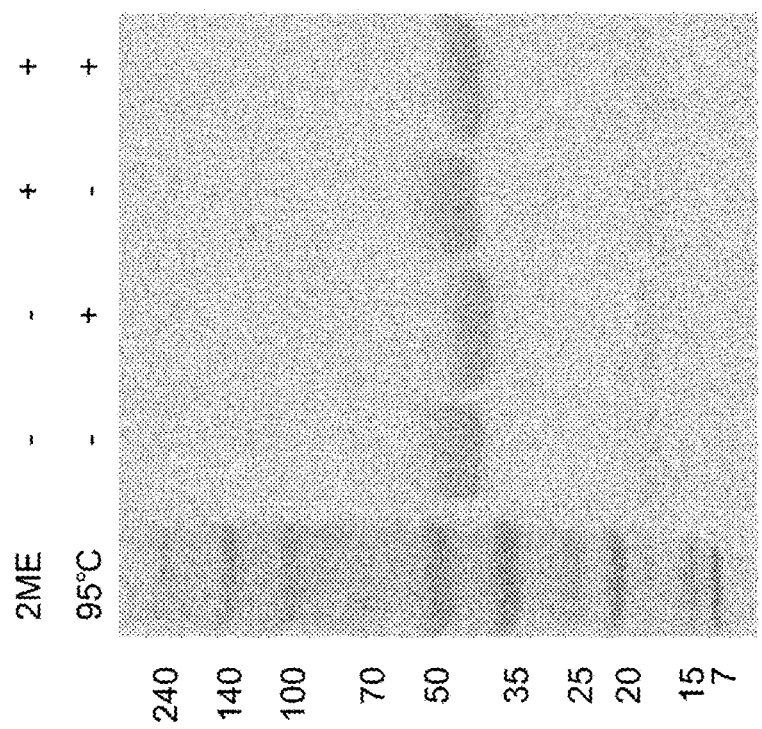
FIG. 3 is a photograph showing an electrophoretic profile of purified BC2LCN-ETA.
Figure 4:
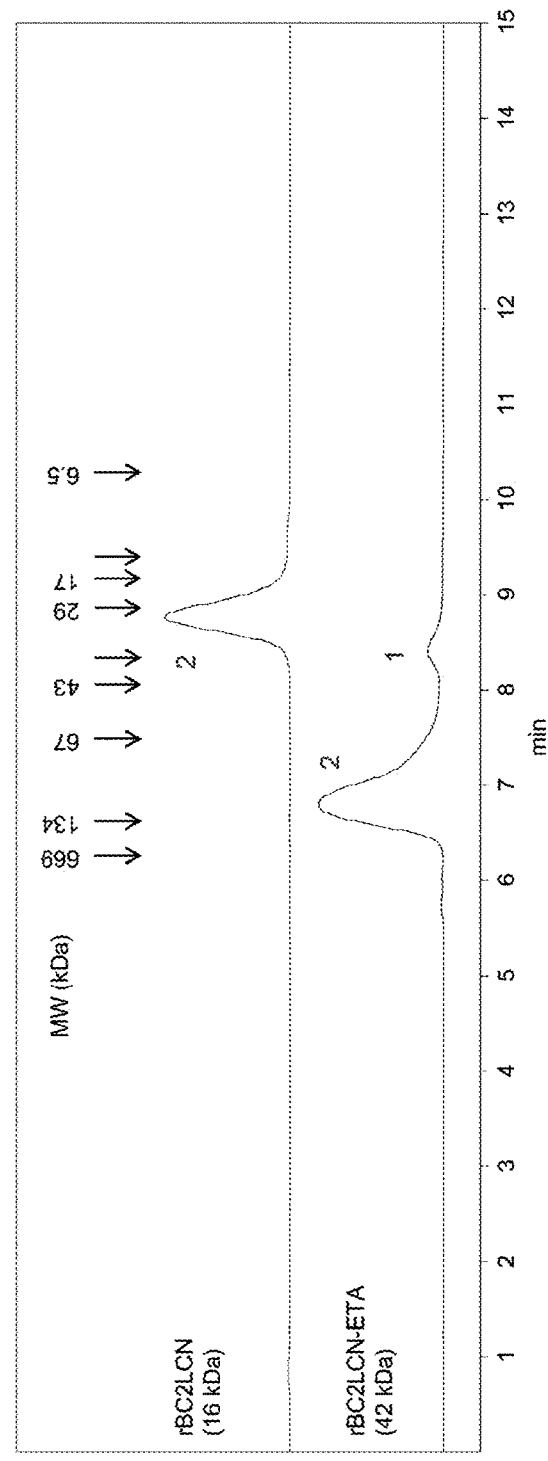
FIG. 4 is a chart showing the results of gel filtration chromatography analysis of rBC2LCN and rBC2LCN-ETA.

To confirm the purification degree, the fractions of flow-through (T), the first washing (W1), the second washing (W2), the third washing (W3), the first fucose elution (E1), the second fucose elution (E2), and the third fucose elution (E3) were subjected to SDSPAGE electrophoresis for confirmation (FIG. 2). In the first elusion fraction, a single band could be confirmed around 42 kDa; and, this molecular weight corresponds to that of a purified rBC2LCN-ETA monomer having the structure of "rBC2LCN-(GSGGG)$_2$-ETA". The purified rBC2LCN-ETA was treated/untreated at 95° C. for 5 minutes in the presence/absence of 2-mercaptoethanol (2-ME) to prepare samples, which were then subjected to SDS-PAGE and then to Coomassie brilliant blue staining (FIG. 3). As a result, the purified rBC2LCN-ETA could be confirmed as a single band of about 42 kDa under each condition. The molecular weight under non-denaturing conditions was analyzed by gel filtration chromatography (FIG. 4). As a result, rBC2LCN-ETA was found to form a dimer, like wild-type rBC2LCN.

Example 2: Binding of rBC2LCN-ETA to Human iPS Cell

Human iPS cells (strain 201B7) used in this Example were obtained from Riken BioResource Center.

The binding affinities of rBC2LCN-ETA and wild-type rBC2LCN to "Fucα1-2Galβ1-3GlcNAc (H type 1)" and "Fucα1-2Galβ1-3GalNAc (H type 3)" as sugar chain ligands for rBC2LCN were examined by frontal affinity chromatography (Non Patent Literature 8). The results are shown below (Table 1). The dissociation constant (Kd value) of rBC2LCN-ETA as a fusion protein was 9.9 μM for H type 1 and 32.3 μM for H type 3, and was found to be comparable to the dissociation constant of wild-type rBC2LCN (8.3 μM for H type 1 and 25.4 μM for H type 3).

TABLE 1

|  | H type1-pNP | H type3-pNP |
|---|---|---|
|  | $K_d$ (μM) | |
| rBC2LCN | 9.9 | 32.3 |
| rBC2LCN-ETA | 8.3 | 25.4 |

Figure 5:
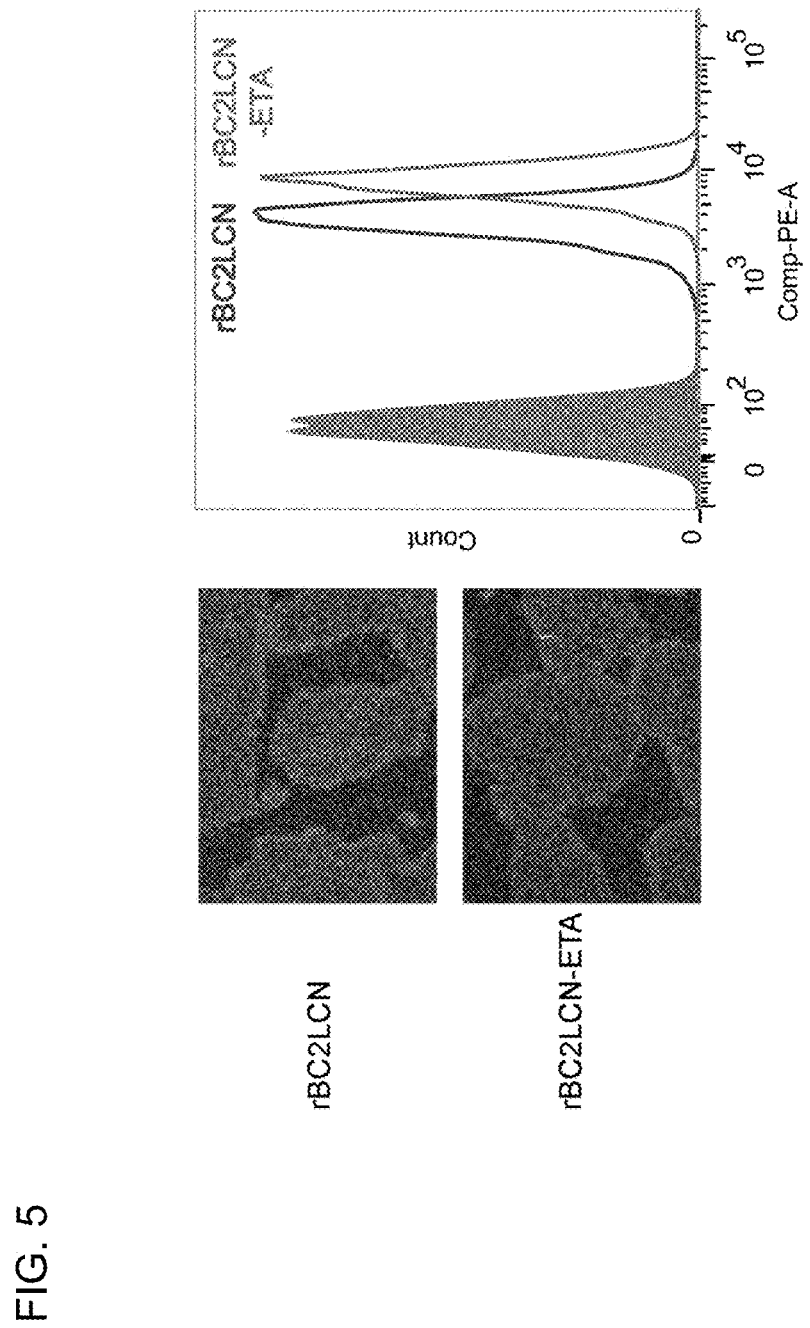
FIG. 5 is a set of drawings showing the binding of rBC2LCN and rBC2LCN-ETA to human iPS cells.

Then, binding to human iPS cells (strain 201B7) was observed by fluorescence staining. Human iPS cells (strain 201B7) cultured in a 24-well plate were fixed with 4% paraformaldehyde at room temperature for 20 minutes, reacted with 10 μg/mL of Cy3-labeled rBC2LCN or Cy3-labeled rBC2LCN-ETA at room temperature for 1 hour, and observed under a fluorescence microscope (left of FIG. 5). As a result, rBC2LCN-ETA was found to be able to stain human iPS cells (strain 201B7) to the same extent as rBC2LCN. Binding to human iPS cells (strain 201B7) was also examined by flow cytometry. Human iPS cells (10$^5$ cells) were reacted with Cy3-labeled rBC2LCN or Cy3-labeled rBC2LCN-ETA at a concentration of 5 μg/mL 4° C. for 1 hour, followed by analysis using flow cytometry (right of FIG. 5). rBC2LCN-ETA was found to be able to stain human iPS cells (strain 201B7) to the same extent as rBC2LCN. The above results showed that rBC2LCN-ETA had almost the same properties as rBC2LCN in terms of binding specificity and binding affinity despite conversion to the fusion protein.

Example 3: Killing Effect of rBC2LCN-ETA on Human ES Cell

Human ES cells (strain H7 (strain WA07)) used in this Example were obtained from Wisconsin International Stem Cell (WISC) Bank. The culture method was according to the protocol of WiCell Research Institute.

Figure 6:
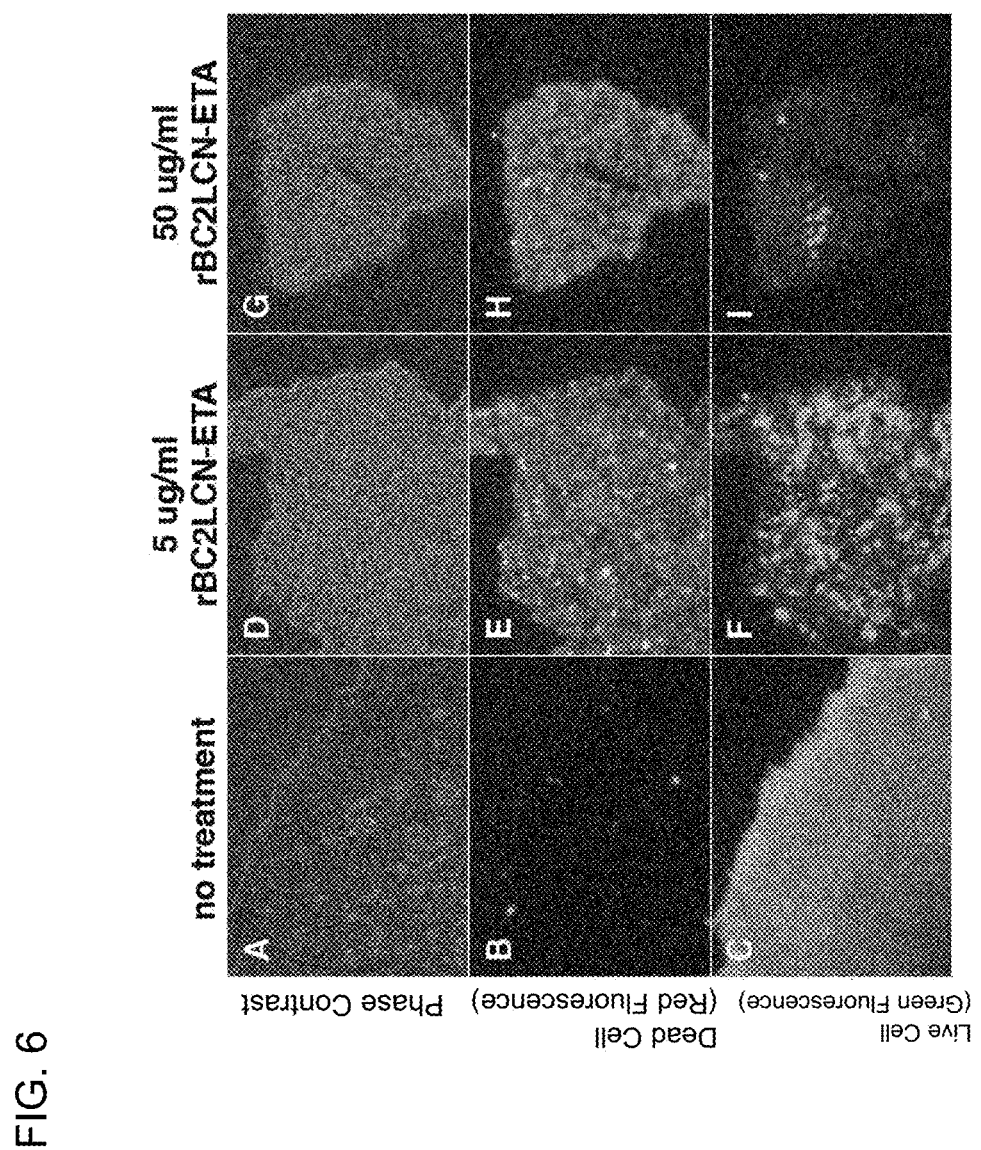
FIG. 6 is a series of photographs showing a killing effect of rBC2LCN-ETA on human ES cells.

Solutions of rBC2LCN-ETA obtained in Example 1 in a dilution series (5 and 50 μg/mL) were prepared and reacted with human ES cells (strain H7 (strain WA07)) during culture. 24 Hours after adding rBC2LCN-ETA, the life or death of the ES cells was determined using LIVE/DEAD Cell Imaging Kit (488/570) (Life Technologies Co., Ltd.) (FIG. 6). When rBC2LCN-ETA was added at concentrations of 5 and 50 μg/mL and phase contrast images were observed 24 hours later, degeneracies were seen in the colonies of the ES cells (FIGS. 6A, D, and G). Live cells decreased concentration-dependently (FIGS. 6C, F, and I. In the figure, the red fluorescence is a label specific for dead cells and the green fluorescence is a label specific for live cells. Hereinafter referred to the same.), and almost all the ES cells died in the group treated with 50 μg/mL rBC2LCN-ETA (FIGS. 6G, H, and I). This confirmed that rBC2LCN-ETA had the ability to kill human ES cells.

Example 4: Killing Effect of rBC2LCN-ETA on Human iPS Cell

Figure 7:
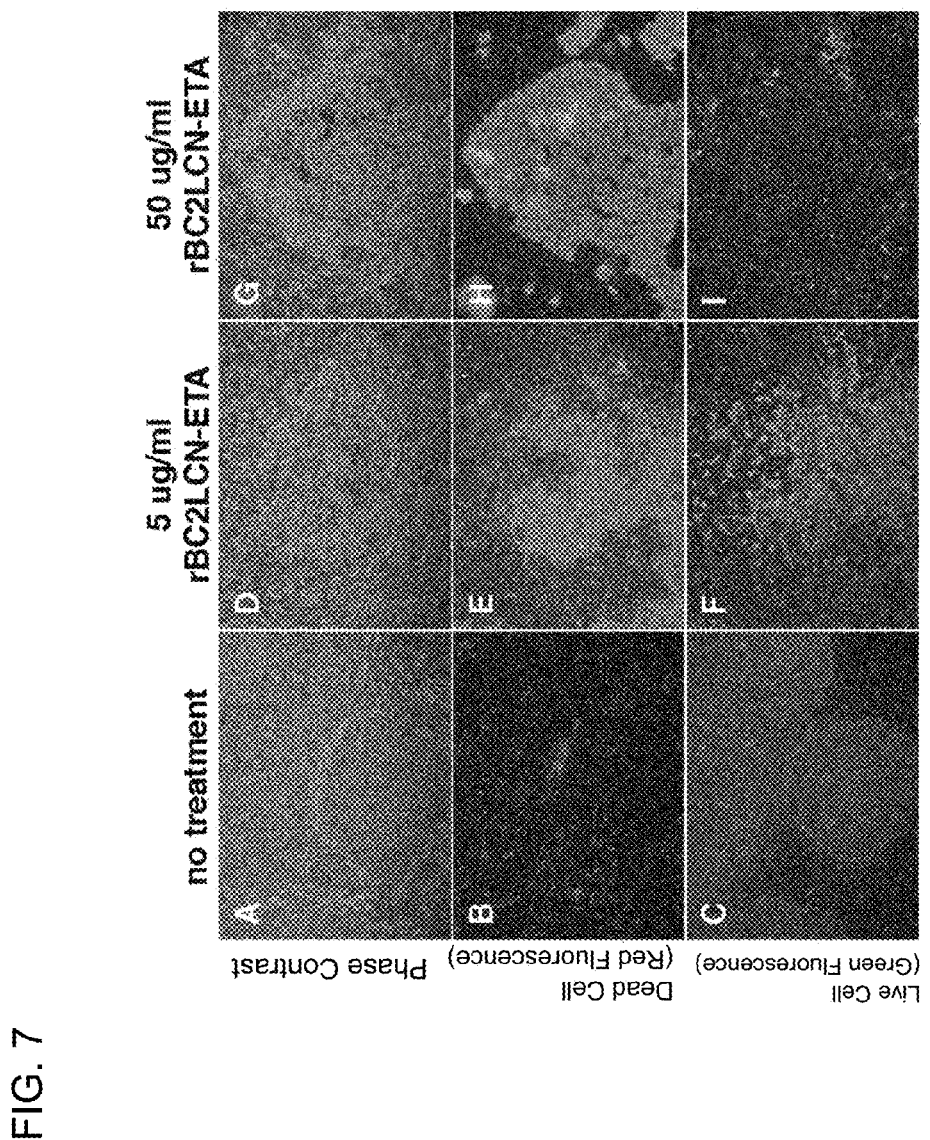
FIG. 7 is a series of photographs showing a killing effect of rBC2LCN-ETA on human iPS cells.

Human iPS cells (strain 201B7) used in this Example were obtained from Riken BioResource Center. Culture was performed using the method of Tateno et al. (Tateno H, et al., (2011) J. Biol. Chem. 286, 20345-20353). Solutions of rBC2LCN-ETA in a dilution series (5 and 50 μg/mL) were prepared and reacted with human iPS cells (strain 201B7) during culture. 24 Hours after adding rBC2LCN-ETA, the life or death of the iPS cells was determined using LIVE/DEAD Cell Imaging Kit (488/570) (Life Technologies Co., Ltd.) (FIG. 7). When rBC2LCN-ETA was added at concentrations of 5 and 50 μg/mL and phase contrast images were observed 24 hours later, degeneracies were seen in the colonies of the iPS cells (FIGS. 7A, D, and G). Live cells decreased concentration-dependently (FIGS. 7C, F, and I), and almost all the iPS cells died in the group treated with 50 μg/mL rBC2LCN-ETA (FIGS. 7G, H, and I). In contrast, circumjacent feeder cells derived from mouse fibroblasts were not killed at all. This confirmed that rBC2LCN-ETA had the ability to kill human iPS cells.

Example 5: Action of rBC2LCN-ETA on Differentiated Cell

Figure 8:
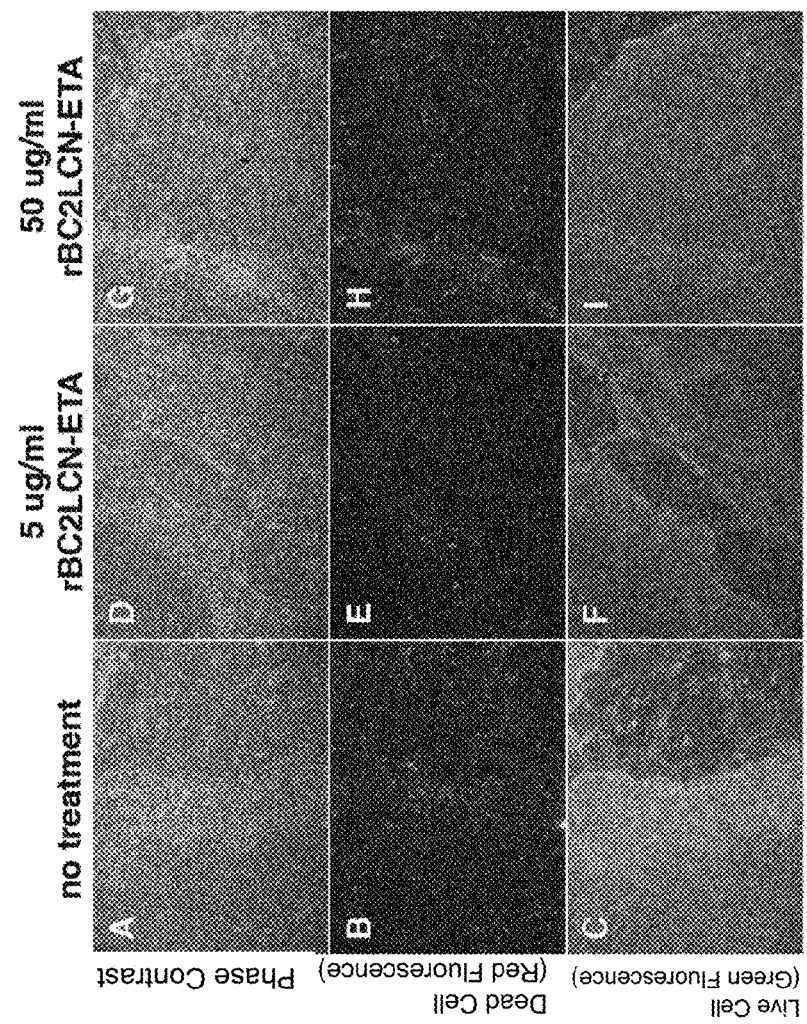
FIG. 8 is a series of photographs showing a killing effect of rBC2LCN-ETA on differentiated cells.

The differentiation of human iPS cells (strain 201B7) was induced by adding retinoic acid to a final concentration of $10^{-5}$ M before culture according to the method of Draper et al. (Draper J S, et al., (2000) J. Anat. 200: 249-58.). The culture was performed for 8 days, and the start of differentiation was confirmed from the morphology of the cells; solutions of rBC2LCN-ETA in a dilution series (5 and 50 μg/mL) were prepared and reacted with the differentiated cells during culture. 24 Hours after adding rBC2LCN-ETA, the life or death of the differentiated cells was determined using LIVE/DEAD Cell Imaging Kit (488/570) (Life Technologies Co., Ltd.) (FIG. 8). When rBC2LCN-ETA was added at concentrations of 0.005 and 0.05 mg/mL and phase contrast images were observed 24 hours later, no effect of addition of rBC2LCN-ETA was observed (FIGS. 8A, D, and G). When LIVE/DEAD Cell Imaging Kit (488/570) was used, no dead cells were also found to increase compared to those for control (FIGS. 8B, C, E, F, H, and I). This confirmed that rBC2LCN-ETA had no ability to kill human differentiated cells.

Example 6: Killing Effect of rBC2LCN-ETA on Human iPS Cell

Figure 9:
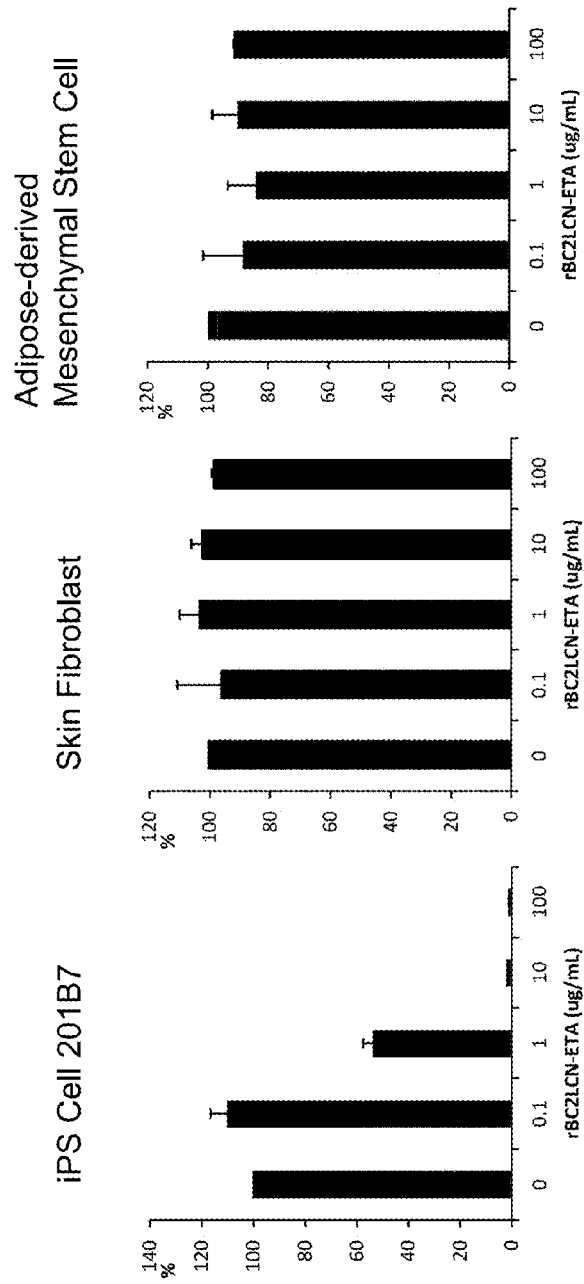
FIG. 9 is a series of graphs showing a killing effect of rBC2LCN-ETA.

Human iPS cells (strain 201B7) used in this Example were obtained from Riken BioResource Center. Solutions of rBC2LCN-ETA in a dilution series (0 to 100 μg/mL) were prepared and each added to a culture medium of human iPS cells (strain 201B7). 24 Hours after adding rBC2LCN-ETA, the life or death of the iPS cells was determined using Cell Counting Kit-8 (Dojindo) (FIG. 9). As a result, live cells were found to decrease concentration-dependently; when the iPS cells were reacted with 10 μg/mL or more of the solution, almost all the iPS cells died 24 hours later. In contrast, for human skin fibroblasts as differentiated cells, having not the sugar chain ("Fucα1-2Galβ1-3GlcNAc/Fucα1-2Galβ1-3GalNAc") recognized by rBC2LCN on the cell surface at all, even the solution having a concentration of as high as 100 μg/mL was found to have no ability to kill cells. For human fat-derived mesenchymal stem cells having a small amount of the sugar chain recognized by rBC2LCN among stem cells, the solution could not exert on the order of 10% of the ability to kill cells until it was administered at a concentration of as high as 100 μg/mL.

Example 7: Action of rBC2LCN-Saporin on Human iPS Cell

Figure 10:
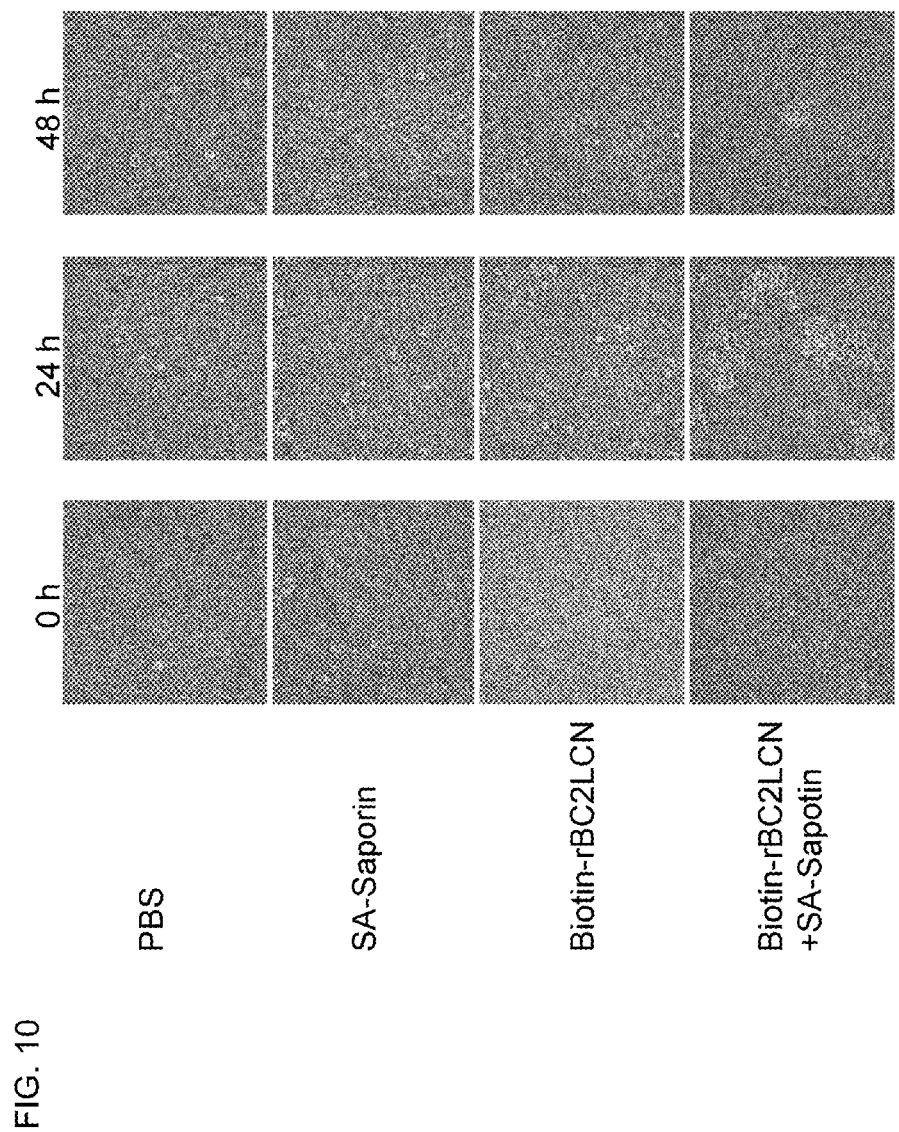
FIG. 10 is a series of photographs showing a killing effect of rBC2LCN-saporin on human iPS cells.

Human iPS cells (strain 201B7) used in this Example were obtained from Riken BioResource Center. PBS alone, streptavidin-saporin (SA-saporin, final concentration: 0.6 μM), biotinylated rBC2LCN (final concentration: 0.6 μM), and a complex of streptavidin-saporin (SA-saporin, final concentration: 0.6 μM) and biotinylated rBC2LCN (final concentration: 0.6 μM) were each added to a culture medium during culture human iPS cells (strain 201B7), and 0, 1, and 2 days later, subjected to phase contrast observation under a microscope (FIG. 10). As a result, whereas PBS alone, streptavidin-saporin alone, and biotinylated rBC2LCN alone little affected human iPS cells, the complex of streptavidin-saporin and biotinylated rBC2LCN caused degeneracy in the colony of human iPS cells 24 hours later. Almost all the cells died 48 hours later. This confirmed that a fusion product of rBC2LCN and saporin through streptavidin-biotin binding also had the ability to kill human iPS cells.

Example 8: Action of FITC-Labeled rBC2LCN on Human iPS Cell

Figure 11:
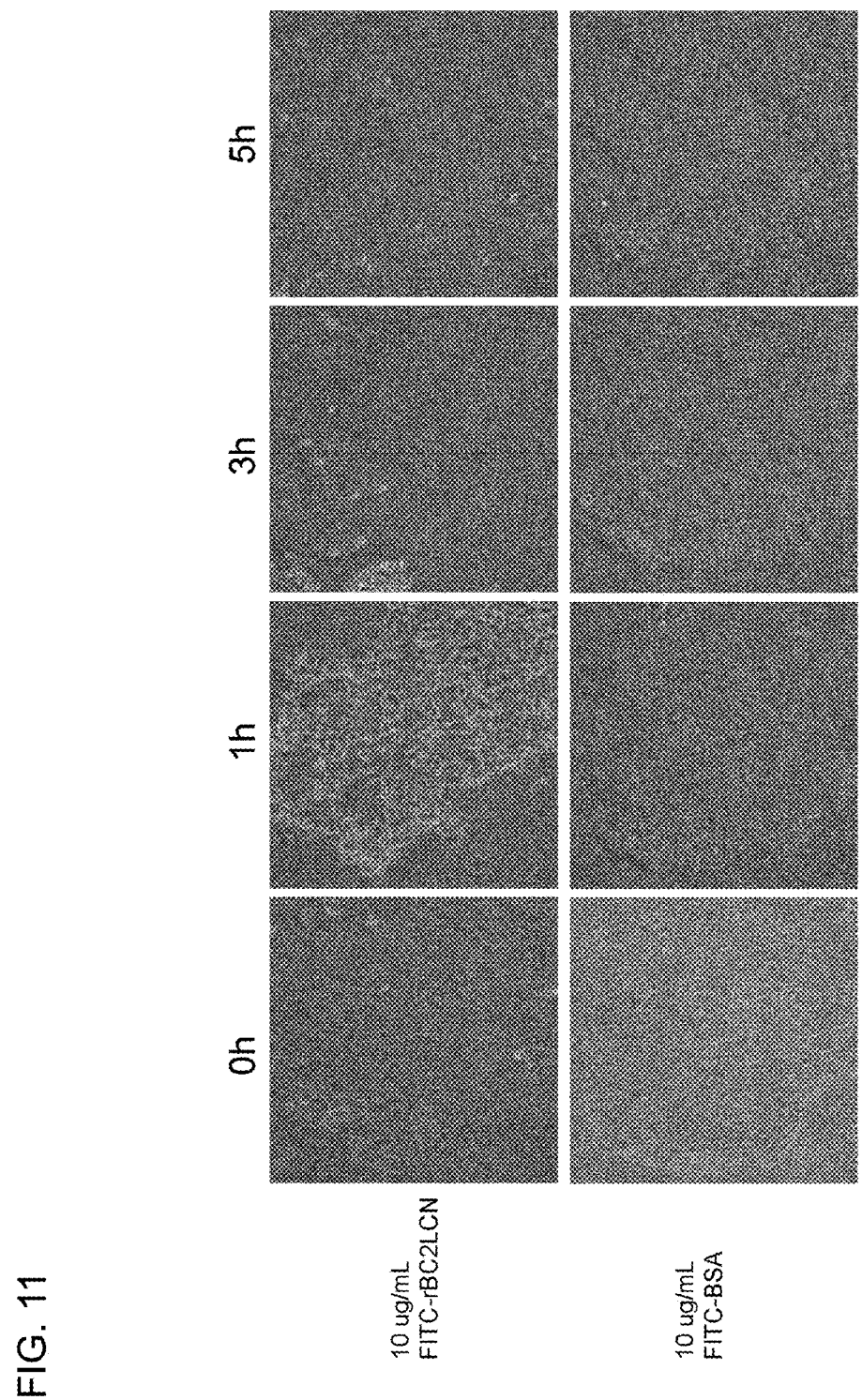
FIG. 11 is a series of photographs showing a killing effect of FITC-labeled rBC2LCN on human iPS cells.

Human iPS cells (strain 201B7) used in this Example were obtained from Riken BioResource Center. FITC-labeled rBC2LCN (10 μg/mL) was added to a culture medium in which the human iPS cells were cultured, and after 1 hour of binding reaction, the resultant was radiated with excitation light for 60 seconds (FIG. 11). The resultant was subjected to phase contrast observation under a microscope 1, 3, and 5 hours later. 6 Hours later, degeneracy was seen in the colony of the human iPS cells, and many of the cells died. FITC-labeled bovine serum albumin (FITC-BSA) used as control was not observed to have a cell-killing effect; thus, the activity of rBC2LCN to bind to human iPS cells was found to be important in killing the human iPS cells. This confirmed that FITC-labeled rBC2LCN had the ability to kill human iPS cells.

Figure 12:
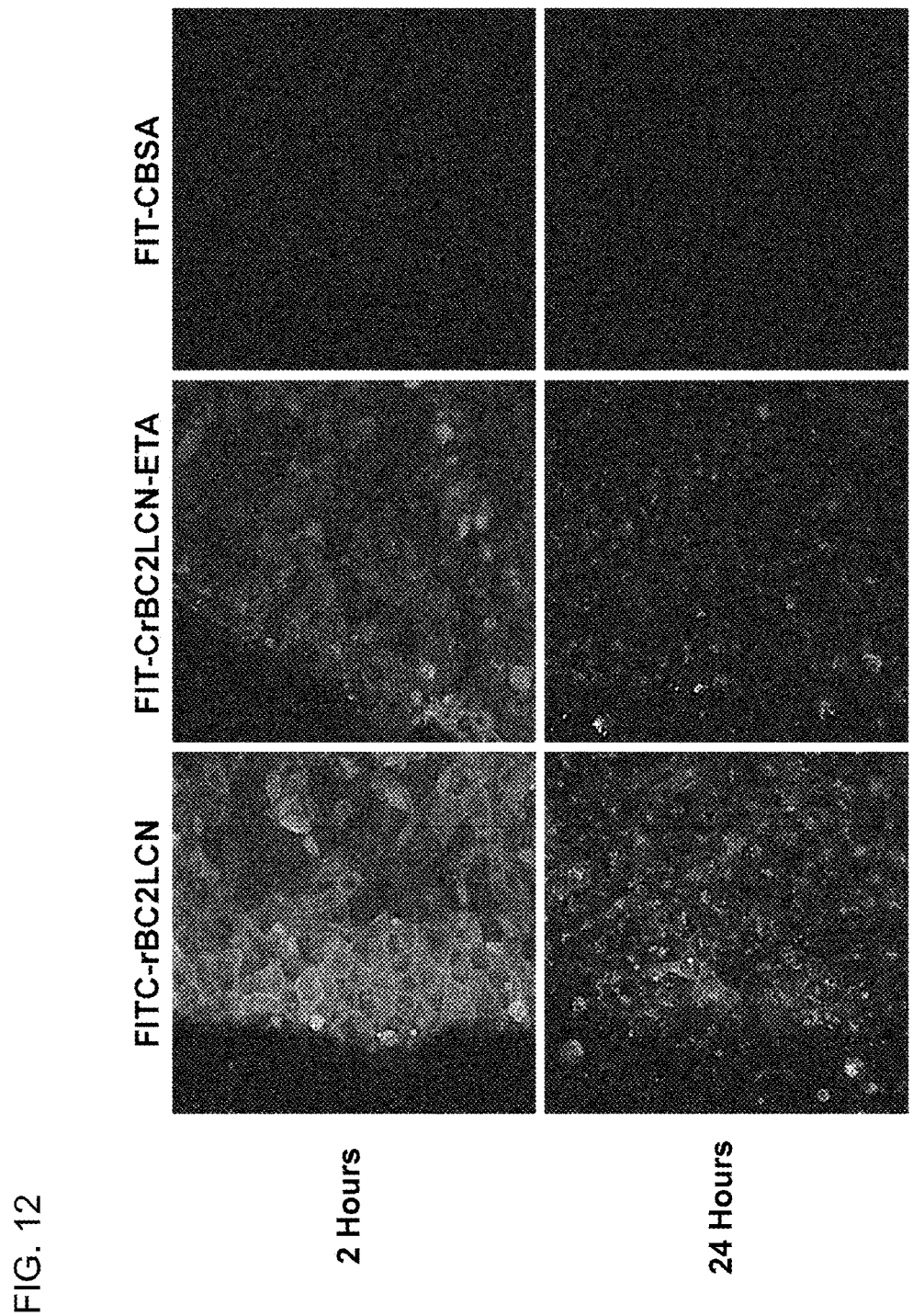
FIG. 12 is a series of photographs showing the internalization of FITC-labeled rBC2LCN and rBC2LCN-ETA into human iPS cells.

Example 9: Internalization of FITC-Labeled rBC2LCN and rBC2LCN-ETA into Human iPS Cell Human iPS cells (strain 201B7) used in this Example were obtained from Riken BioResource Center. FITC-labeled rBC2LCN or FITC-labeled rBC2LCN-ETA was added at a concentration of 1 μg/mL to a culture medium of the human iPS cells (strain 201B7), which was then reacted at 37° C. for 2 hours; immediately (2 hours) and 24 hours after reaction, the resultant was irradiated with excitation light and subjected to confocal microscope observation under a microscope (FIG. 12). Because this Example was an experiment for observing cell internalization, irradiation conditions were kept at the minimum level enabling photography (scan speed: 12.5 μs/pixel and laser output: 1%) in order to avoid the ability of FITC to kill undifferentiated cells due to the long-time irradiation with the excitation light.

Immediately after replacement with a new medium containing no FITC-labeled rBC2LCN, the cell surface was clearly stained (upper left). In addition, 2 hours later, the staining of the cell surface was lighter, and 24 hours later, staining in dots was observed in the cells, showing that the FITC-labeled rBC2LCN was taken up in the cells (lower left). In contrast, for FITC-labeled BSA used as control, binding to the human iPS cells could not be confirmed (right). A case where rBC2LCN-ETA as an ETA fusion product was labeled with FITC (middle) is shown together. It will be seen how the FITC-labeled rBC2LCN-ETA is rapidly taken up in the cells as well as that the death of the iPS cells progresses due to the cell-killing effect of the internalized ETA 24 hours later.

Figure 13:
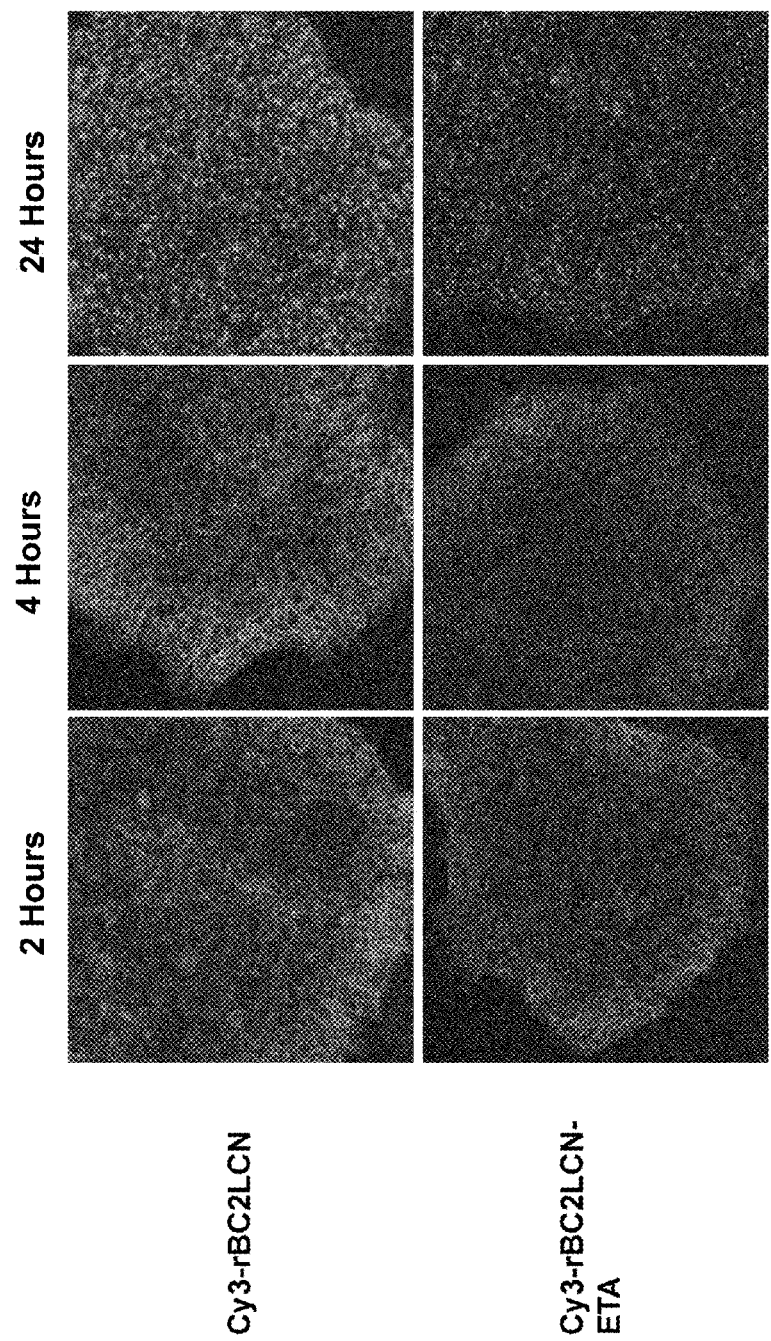
FIG. 13 is a series of photographs showing the internalization of Cy3-labeled rBC2LCN and rBC2LCN-ETA into human iPS cells.

Example 10: Internalization of Cy3-Labeled rBC2LCN and rBC2LCN-ETA into Human iPS Cell Human iPS cells (strain 201B7) used in this Example were obtained from Riken BioResource Center. Cy3-labeled rBC2LCN was added at a concentration of 1 μg/mL to a culture medium of the human iPS cells (strain 201B7), which was then reacted at 37° C. for 2 hours; immediately (2 hours), 4 hours, and 24 hours after reaction, the resultant was irradiated with excitation light for phase contrast observation under a microscope (FIG. 13). Immediately after replacement with a new medium containing no Cy3-labeled rBC2LCN, the cell surface was clearly stained (left). In addition, 2 hours later, staining in dots could be confirmed in the cells (middle). 24 Hours later, staining in dots was clearly observed in the cells, showing that the Cy3-labeled rBC2LCN was taken up in the cells. Similarly, Cy3-labeled rBC2LCN-ETA was shown to be internalized into the cells. Because even with different fluorescent forms of FITC and Cy3, rBC2LCN was confirmed to be internalized into the cells, internalization into the human iPS cells was demonstrated not to depend on the type of the compound fused to rBC2LCN but to be the effect of rBC2LCN.

REFERENCE TO A "SEQUENCE LISTING," A TABLE, OR A COMPUTER PROGRAM LISTING APPENDIX SUBMITTED AS AN ASCII TEXT FILE

The material in the ASCII text file, named "PSK-9027US-Sequence-Listing-revised.txt", created Aug. 5, 2015, file size of 8,192 bytes, is hereby incorporated by reference.

The invention claimed is:

1. A method for introducing a protein toxin or a dye into mammalian pluripotent stem cells, comprising:
   chemically or electrically fusing the protein toxin or the dye to rBC2LCN to obtain an rBC2LCN-toxin fusion protein or an rBC2LCN-dye protein, and
   contacting the rBC2LCN-toxin fusion protein or the rBC2LCN-dye protein with the mammalian pluripotent stem cells in vitro such that the protein toxin or the dye is introduced into the mammalian pluripotent stem cells, wherein the protein toxin is a protein or a domain thereof that has an ability to kill cells.

2. The method according to claim 1, wherein the protein toxin has a protein synthesis-inhibiting action in cells.

3. The method according to claim 1, wherein the contacting of the mammalian pluripotent stem cells with the rBC2LCN-toxin fusion protein results in killing the mammalian pluripotent stem cells.

4. A method for preparing cells for transplantation comprising:
   (a) differentiating mammalian pluripotent stem cells in vitro; and
   (b) contacting the cells obtained in step (a) with an rBC2LCN-toxin fusion protein, in which a protein toxin and rBC2LCN are chemically or electrically fused to each other, in vitro such that the mammalian pluripotent stem cells are eliminated, thereby preparing the cells for transplantation, wherein the protein toxin is a protein or a domain thereof that has an ability to kill cells.

5. The method according to claim 4, wherein the protein toxin has a protein synthesis-inhibiting action in cells.

* * * * *